US008927506B2

(12) United States Patent
Priebe et al.

(10) Patent No.: US 8,927,506 B2
(45) Date of Patent: Jan. 6, 2015

(54) ACETATES OF 2-DEOXY MONOSACCHARIDES WITH ANTICANCER ACTIVITY

(75) Inventors: Waldemar Priebe, Houston, TX (US); Marcin Cybulski, Warsaw (PL); Izabela Fokt, Houston, TX (US); Stanislaw Skora, Houston, TX (US); Charles Conrad, Spring, TX (US); Timothy Madden, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/003,429

(22) PCT Filed: Jun. 25, 2009

(86) PCT No.: PCT/US2009/048675

§ 371 (c)(1), (2), (4) Date: Mar. 3, 2011

(87) PCT Pub. No.: WO2010/005799

PCT Pub. Date: Jan. 14, 2010

(65) Prior Publication Data

US 2011/0160151 A1 Jun. 30, 2011

Related U.S. Application Data

(60) Provisional application No. 61/079,968, filed on Jul. 11, 2008.

(51) Int. Cl.

| | |
|---|---|
| ***A61K 31/70*** | (2006.01) |
| ***C07H 1/00*** | (2006.01) |
| ***C07H 15/00*** | (2006.01) |

(52) U.S. Cl.

CPC .................................... *A61K 31/70* (2013.01)

USPC ................ 514/23; 514/25; 536/1.11; 536/4.1

(58) Field of Classification Search

USPC ................................................ 536/1.11, 4.1

See application file for complete search history.

(56) References Cited

U.S. PATENT DOCUMENTS

| | | | |
|---|---|---|---|
| 4,464,530 | A | 8/1984 | Matsumura et al. |
| 6,319,695 | B1 | 11/2001 | Wong et al. |
| 6,670,330 | B1 | 12/2003 | Lampidis et al. |
| 6,894,033 | B2 | 5/2005 | Cruz et al. |
| 6,906,048 | B2 | 6/2005 | Davis et al. |
| 6,979,675 | B2 | 12/2005 | Tidmarsh |
| 7,001,888 | B2 | 2/2006 | Tidmarsh et al. |
| 8,299,033 | B2 | 10/2012 | Priebe et al. |
| 2004/0167079 | A1 | 8/2004 | Tidmarsh et al. |
| 2005/0043250 | A1 | 2/2005 | Lampidis et al. |
| 2005/0143336 | A1 | 6/2005 | Ramesh et al. |
| 2007/0292478 | A1 | 12/2007 | Youri |
| 2010/0130434 | A1 | 5/2010 | Priebe et al. |
| 2011/0003758 | A1 | 1/2011 | Priebe et al. |

FOREIGN PATENT DOCUMENTS

| | | | |
|---|---|---|---|
| CN | 1196059 | | 10/1998 |
| EP | 1881000 | A1 | 1/2008 |
| JP | 56103197 | | 8/1981 |
| WO | 97/00882 | | 1/1997 |
| WO | WO97/00882 | A1 | 1/1997 |
| WO | 01/82926 | | 11/2001 |
| WO | WO 03-018598 | | 3/2003 |
| WO | WO 2004-108166 | | 12/2004 |
| WO | WO 2007-100728 | | 9/2007 |
| WO | WO 2010-005799 | | 1/2010 |
| WO | WO 2012-142615 | | 10/2012 |

OTHER PUBLICATIONS

Hennen, W.J., et al., Enzymes in Carbohydrate Synthesis: Lipase-Catalyzed Selection Acylation and Deacylation of Furanose and Pyranose Derivatives, Journal Organic Chemistry, American Chem Society, vol. 53, (1988).

Huang, X., et al., Hydrosis of (2-Deoxy-beta-D-glucopyranosyl) Pyridinium Salts, J. Am. Chem Soc, 117(43) (1995).

EPO Communication Extended Supplementary Search Report and Search Opinion EP 09 79 4965, Mar. 22, 2012.

Garber, Ken, Energy Boost: The Warburg Effect Returns in a New Theory of Cancer, Journal of the National Cancer Institute, vol. 96, No. 24, 1805-1806 , Dec. 15, 2004.

Lu, H., et al., Hypoxia-inducible Factor 1 Activation by Aerobic Glycolysis Implicates the Warburg Effect in Carcinogenesis, J. Bio. Chem. vol. 277, No. 26, 23111 (2002).

Klionsky, D.J., et al., Autophagy as a Regulated Pathway of Cellular Degradation, Science, 290:1717-1721, (2000).

Cuervo, A.M., Autophagy: In Sickness and in Health, Trends Cell Biol, 14: 70-77, ( 2004).

Shintani, T., et al., Autophagy in Health and Disease: A Double-Edged Sword, Science, 306: 990-995, (2004).

Bursch, W., et al., Programmed Cell Death (PCD). Apoptosis, Autophagic PCD, or Others? Ann. N.Y. Acad. Sci., 926:1-12, (2000).

Ogier-Denis, E., et al., Autophagy: A Barrier or an Adaptive Response to Cancer, Biochim Biophys Acta, 1603:113-128, (2003).

Gozuacik, D., et al., Autophagy as a Cell Death and Tumor Suppressor Mechanism, Oncogene, 23: 2891-2906, (2004).

Liang, X.H., et al., Induction of Autophagy and Inhibition of Tumorigenesis by Beclin 1, Nature, 402: 672-676, (1999).

Qu, X., et al., Promotion of Tumorigenesis by Heterozygous Disruption of the Beclin 1 Autophagy Gene, J Clin Invest, 112:1809-1820, (2003).

Yue. Z., et al., Beclin 1, an Autophagy Gene Essential for Early Embryonic Development, Is a Haploinsufficient Tumor Suppressor, Proc Natl Acad Sci USA, 100: 15077-15082, (2003).

Altan, N., et al., Defective Acidification in Human Breast Tumor Cells and Implications for Chemotherapy, J Exp Med, 187: 1583-1598, (1998).

Paglin, S., et al., A Novel Response of Cancer Cells to Radiation Involves Autophagy and Formation of Acidic Vesicles, Cancer Res, 61: 439-444, (2001).

Kanzawa, T., et al., Induction of Autophagic Cell Death in Malignant Glioma Cells by Arsenic Trioxide, Cancer Res, 63:2103-2108, (2003).

Daido, S., et al., Inhibition of the DNA-Dependent Protein Kinase Catalytic Subunit Radiosensitizes Malignant Glioma Cells by Inducing Autophagy, Cancer Res, 65:4368-4375, (2005).

(Continued)

*Primary Examiner* — Elli Peselev

(74) *Attorney, Agent, or Firm* — Dennis A. Bennett

(57) ABSTRACT

Novel compounds and methods of using the same to inhibit glycolysis and treat cancer and other diseases are provided herein.

8 Claims, 3 Drawing Sheets

(56) References Cited

OTHER PUBLICATIONS

Takeuchi, H., et al., Synergistic Augmentation of Rapamycin-Induced Autophagy in Malignant Glioma Cells by Phosphatidylinositol 3-Kinase/Protein Kinase B Inhibitors, Cancer Res, 65:3336-3346, (2005).

Edinger, A.L., et al. Defective Autophagy Leads to Cancer, Cancer Cell, 4:422-424, (2003).

Kondo, Y., et al., Role of Autophagy in Cancer Development and Response to Therapy, Nat Rev Cancer, 5:726-734, (2005).

Hait, W.N., et al., A Matter of Life or Death (or Both): Understanding Autophagy in Cancer, Clin Cancer Res., Apr. 1, 12(7 Pt 1):1961-5, (2006).

Munafo, D.B., et al., A Novel Assay to Study Autophagy: Regulation of Autophagosome Vacuole Size by Amino Acid Deprivation, J Cell Sci, 114:3619-29, (2001).

Kabeya, Y., et al., LC3, a Mammalian Homologue of Yeast Apg8p, Is Localized in Autophagosome Membranes After Processing, EMBO J, 19:5720-5728, (2000).

Mizushima, N., et al., Dissection of Autophagosome Formation Using Apg5-Deficient Mouse Embryonic Stem Cells, J Cell Biol, 152:657-668, ( 2001).

Beis,I., et al., The Contents of Adenine Nucleotides, Phosphagens and some Glycolytic Intermediates in Resting Muscles from Vertebrates and Invertebrates, Biochem. J. 152, 23-32, (1975).

International Preliminary Report on Patentability dated Jan. 20, 2011.

"Brain Tumors," Merck Manual Online Edition, retrieved May 11, 2011, from the Internet at http://www.merckmanuals.com, revision Feb. 2008.

"Cancer treatment principles," Merck Manual Online Edition, retrieved Feb. 21, 2011, from the Internet at http://www.merckmanuals.com/ , revision Aug. 2007.

"What you need to know about cancer of the pancreas," *National Cancer Institute, National Institutes of Health*, 48 pages, Sep. 2010.

Adam et al., "Synthesis and preliminary evaluation of [$^{18}$F]-deoxy-2,2-difluoro-glucose as apotential PET imaging agent," *J. Labelled Cpd. Radiopharm.*, 42:809-813, 1999.

Adamson et al., "2-deoxy-2,2-difluoro-D-*arabino*-hexose ("2,2-difluoroglucose")," *Carbohyd. Res.*, 18:345-347, 1971.

Aft et al., "Enhancing targeted radiotherapy by copper(II)diacetyl-bis($N^4$-methylthiosemicarbazone) using 2-Deoxy-D-glucose," *Cancer Resesarch*, 63:5496-5504, 2003.

Bessell et al., "Some in vivo and in vitro antitumour effects of the deoxyfluoro-D-gluco-phyranoses," *Europ. J. Cancer*, 9:463-470, 1973.

Bessell et al., "The use of deoxyfluoro-D-glucopyranoses and related compounds in a study of yeast hexokinase sepcficity," *Biochem. J.*, 128:199-204, 1972.

Costantino et al., "A mild and easy one-pot procedure for the synthesis of 2-deoxysugars from glycals," *Tetrahedron Letters*, 41:9177-9180, 2000.

Danishefsky et al., "The total synthesis of avermectin $A_{1a+}$ new protocols for the synthesis of novel 2-deoxypyranose systems and their axial glycosides," *J. Am. Chem. Soc.*, 109:8119-8120, 1987.

Finch and Merchant, "The substrate specificity of yeast hexokinase: reaction with D-arabinose oxime," *Carbohyd. Res.*, 76:225-232, 1979.

Fleming et al., "Molecular consequences of silencing mutant K-*ras* in pancreatic cancer cells: justification for K-*ras*-directed therapy," *Mol Cancer Res*, 3(7):413-423, 2005.

Fowler et al., "Agents for the armamentarium of regional metabolic measurement in vivo via metabolic trapping: $^{11}$C-2-Deoxy-D-glucose and halogenated deoxyglucose derivatives," *Journal of Labelled Compounds and Radiopharmaceuticals*, 16(1):7-9, 1979.

Gatenby and Gillies, "Why do cancers have high aerobic glycolysis?" *Nature Reviews*, 4:891-899, 2004.

Gatley, "Labeled glucose analogs in the genomic era," *The Journal of Nuclear Medicine*, 44(7):1082-1086, 2003.

Gould et al., "Expression of human glucose transporters in *Xenopus* oocytes: kinetic characterization and substrate specificities of the erythrocyte, liver, and brain isoforms," *Biochemistry*, 30:5139-5145, 1991.

Gove et al., Webster's Third New International Dictionary, p. 1798, 1963.

Greene et al., "Protection for the hydroxyl group, including 1,2- and 1,3-diols," *Protective Groups in Organic Synthesis, Third Edition*, 48 pages, 1999.

Kim et al., "Auranofin blocks interleukin-6 signalling by inhibiting phosphorylation of JAK1 and STAT3," *Immunology*, 122(4):607-614, 2007.

Kojima et al., "Metabolic pathway of 2-deoxy-2-fluoro-D-glucose and 2-deoxy-2-fluoro-D-mannose in mice bearing sarcoma 180 studied by fluorin-19 nuclear magnetic resonance," *Chem. Pharm. Bull.*, 36(3):1194-1197, 1988.

Kurtoglu et al., "Under normoxia, 2-deoxy-D-glucose elicits cell death in select tumor types not by inhibition of glycolysis but by interfering with N-linked glycosylation," *Mol. Cancer Ther.*, 6(11):3049-3058, 2007.

Lampidis et al., "Efficacy of 2-halogen substituted D-glucose analogs in blocking glycolysis and killing 'hypoxic tumor cells'," *Cancer Chemother Pharmacol*, 58:725-734, 2006.

Lampidis et al., "Growth inhibitory effects of 2-halo analogs of 2-deoxy-D-glucose on hypoxic tumor cells," Abstract Submission, 04-AB-4359-AACR, 2003.

Liu and Wong, "Enzymatic halohydration of glycals," *J. Org. Chem.*, 57(13):3748-3750, 1992.

McCarter et al., "Syntheses, radiolabelling, and kinetic evaluation of 2-deoxy-2-fluoro-2-iodo-D-hexoses for medical imaging," *Carbohydrate Research*, 266:273-277, 1995.

Mohanti et al., "Improving cancer radiotherapy with 2-deoxy-D-glucose: phase I/II clinical trials on human cerebral gliomas," *Int. J. Radiation Oncology Biol. Phys.*, 35(1):103-111, 1996.

Morin, Procurement of 2-deoxy-2-iodo-D-glucose (2-DIG), *Tetrahedron Letters*, 47:5055-5058, 2006.

O'Connell and London, "Identification of 2-fluoro-2-deoxy-D-glucose metabolites by $^{19}$F{$^{1}$H} hetero-RELAY," *Journal of Magnetic Resonance*, Series B, 109:264-269, 1995.

Office Action and Search Report issued in Chinese Application No. 200980135924, issued Dec. 27, 2012.

Office Action issued in Chinese Application No. 200980135924, issued Jan. 29, 2012.

Office Action issued in U.S. Appl. No. 12/920,104, mailed Jan. 7, 2013.

Office Action issued in U.S. Appl. No. 12/920,104, mailed Jun. 15, 2012.

PCT International Search Report and Written Opinion issued in International Application No. PCT/US2012/033837, mailed Nov. 29, 2012.

Pelican et al., "Glycolysis inhibition for anticancer treatment," *Oncogene*, 25:4633-4646, 2006.

Roush and Narayan, "2-deoxy-2-iodo-α-mannopyranosyl and -talopyranosyl acetates: highly stereoselective glycosyl donors for the synthesis of 2-deoxy-α-glycosides," *Organic Letters*, 1(6):899-902, 1999.

Yang et al., "Further metabolic studies of indole and sugar derivatives using the staurosporine producer *Streptomyces staurosporeus," J. Nat. Prod.*, 60:230-235, 1997.

ACETATES OF 2-DEOXY MONOSACCHARIDES WITH ANTICANCER ACTIVITY

CROSS-REFERENCE TO RELATED APPLICATIONS

This application is a national phase application under 35 U.S.C. §371 of International Application No. PCT/US2009/048675, filed Jun. 25, 2009, which claims priority to U.S. Provisional Application No. 61/079,968, filed Jul. 11, 2008.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

BACKGROUND OF THE INVENTION

Reliance on glycolysis has been correlated with disease progression in cancer, and as well as a consistent and significant increase in activity of hexokinase, phosphofructokinase and pyruvate kinase. Hypoxia is also a feature of many solid cancers and has been linked to malignant transformation, metastasis and treatment resistance. Furthermore, glycolysis in cancer cells can be enhanced by certain oncogenes through the increased expression of glucose transporters and glycolytic enzymes found on tumor cells.

Malignant gliomas are the most common subtype of primary brain tumors and the deadliest human cancers. In its most aggressive manifestation, glioblastoma multiforme (GBM), the median survival duration for patients ranges from 9 to 12 months, despite maximum treatment efforts. In fact, approximately one-third of patients with GBM their tumors will continue to grow despite treatment with radiation and chemotherapy.

A serious disadvantage of treating glioblastoma is the harmful effects on normal cells and tissue. Mutagenic potential of certain neoplasmic therapies often promotes tumor resistance and can initiate other malignancies. Tumors can also develop resistance to various other treatments, such as anti-angiogenic therapy. A need exists, therefore, for cancer treatments for highly glycolytic cancer cells such as glioblastoma with little or no toxicity towards normal cells.

SUMMARY OF THE INVENTION

Compounds useful to treat tumors and tumor cell growth including primary tumors such as glioblastoma or high-grade gliomas, high-grade solid tumors, high-grade lymphomas, high-grade hematologic malignancies and secondary brain tumors such as metastatic brain tumors are presented herein. Methods of inhibiting glycolysis using these compounds are further provided. In addition, methods for the treatment of cancer, such as brain and pancreatic cancer, and other diseases including Parkinson's Disease and seizures are described herein. The methods comprise the step of administering to a patient in need thereof a therapeutically effective amount of a compound of the Formula I as follows:

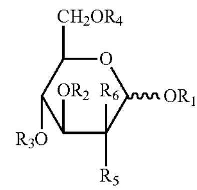

or a salt, ester or prodrug thereof, wherein $R_1$, $R_2$, $R_3$ and $R_4$ are each independently H, $COCH_3$, $COCH_2CH_3$, or $COCH_2CH_3CH_3$;

and $R_5$ and $R_6$ are each independently H or F ($^{18}F$ or $^{19}F$).

BRIEF DESCRIPTION OF THE DRAWINGS

The foregoing summary as well as the following detailed description of the preferred embodiment of the invention will be better understood when read in conjunction with the appended drawings. It should be understood, however, that the invention is not limited to the precise arrangements and instrumentalities shown herein.

For a more complete understanding of the present invention, and the advantages thereof, reference is now made to the following descriptions taken in conjunction with the accompanying drawings, in which.

DETAILED DESCRIPTION

Figure 1:
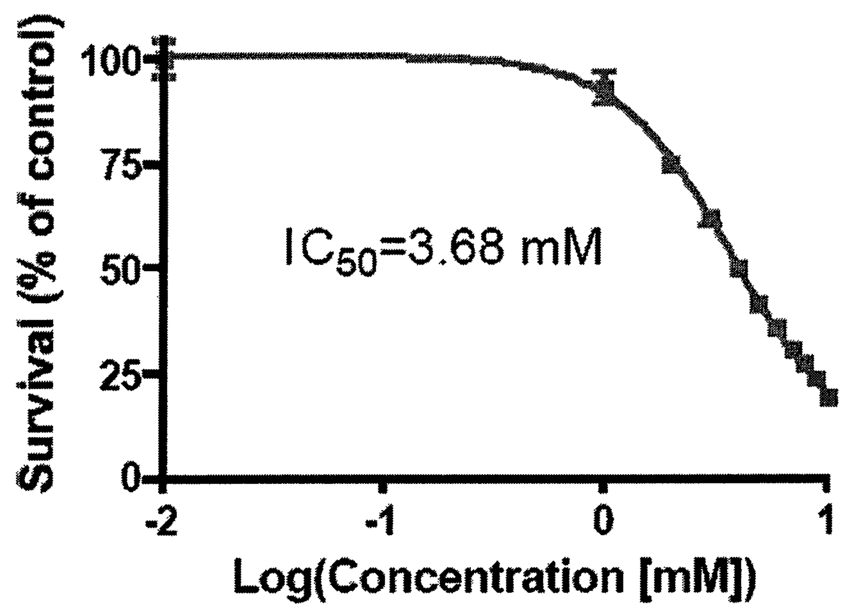
FIG. 1 shows in vitro activity of the compound of Example 1 in U87 glioblastoma cell line.

Compounds useful in treating tumors and tumor cell growth including primary tumors such as glioblastoma or high-grade gliomas, high-grade solid tumors, high-grade lymphomas, high-grade hematologic malignancies and secondary brain tumors such as metastatic brain tumors are provided herein. The compounds presented herein may also be used as a diagnostic for determining whether a subject has cancer or another type of disease. The compounds are also useful to inhibit glycolysis.

The methods presented herein include the step of administering to a subject in need thereof a therapeutically effective amount of a compound of Formulas I as follows:

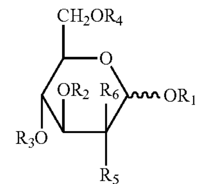

or a salt, ester or prodrug thereof;

wherein $R_1$, $R_2$, $R_3$ and $R_4$ are each independently H, $COCH_3$, $COCH_2CH_3$, or $COCH_2CH_3CH_3$;

and $R_5$ and $R_6$ are each independently H or F ($^{18}F$ or $^{19}F$).

Cells in eukaryotic organisms require energy to carry out cellular processes. Such energy is mainly stored in the phosphate bonds of adenosine 5'-triphosphate ("ATP"). pathways that generate energy in eukaryotic organisms include: (1) glycolysis; (2) the Krebs Cycle (also referred to as the TCA cycle or citric acid cycle); and (3) oxidative phosphorylation. For ATP to be synthesized, carbohydrates are first hydrolyzed into monosaccharides (e.g., glucose), and lipids are hydrolyzed into fatty acids and glycerol. Likewise, proteins are hydrolyzed into amino acids. The energy in the chemical bonds of these hydrolyzed molecules are then released and harnessed by the cell to form ATP molecules through numerous catabolic pathways.

Reliance on glycolysis has been correlated with disease progression in cancer as well as a consistent and significant increase in activity of hexokinase, phosphofructokinase and pyruvate kinase. Hypoxia is found in certain solid cancers and has been linked to angiogenesis, differential tumor growth, malignant transformation, metastasis and treatment resistance. Aerobic glycolysis is often enhanced by certain oncogenes through the increased expression of glucose transporters and glycolytic enzymes found on tumor cells.

Specifically, glucose is a simple sugar or monosaccharide, and the primary source of energy for animals. Glucose is an important sugar in human metabolism having a normal concentration of about 0.1% (usually 60 to 110 mgs per dl) in human blood except in persons suffering from diabetes. As a primary energy source, glucose requires no digestion.

The oxidation of glucose contributes to a series of complex biochemical reactions which provide the energy needed by cells. When oxidized (metabolized) in the body, glucose produces carbon dioxide, water and certain nitrogen compounds. Energy from glucose oxidation is used to convert ADP to adenosine 5'-triphosphate ("ATP"), a multifunctional nucleotide that is known as "molecular currency" of intracellular energy transfer.

ATP produced as an energy source during cellular respiration is consumed by different enzymes and cellular process including biosynthetic reactions, motility and cell division. For signal transduction pathways, ATP is the substrate by which kinases phosphorylate proteins and lipids and adenylate cyclase produces cyclic AMP.

ATP is an unstable molecule that tends to be hydrolyzed in water. Thus, if ATP and ADP are allowed to come into chemical equilibrium, almost all the ATP will be converted to ADP. Cells maintain ATP to ADP at a point ten orders of magnitude from equilibrium, with ATP concentrations a thousand fold higher than the concentration of ADP. This displacement from equilibrium means that the hydrolysis of ATP in the cell releases a lot of energy. Nicholls D. G. & Ferguson S. J. (2002) *Bioenergetics Academic Press* $3^{rd}$ Ed. ATP concentration inside the cell is typically 1-10 mM. Beis I., & Newsholme E. A. (1975) Biochem J 152, 23-32.

ATP is produced by redox reactions using simple sugars (e.g., glucose), complex sugars (carbohydrates), lipids, and proteins. For ATP to be synthesized, carbohydrates are hydrolyzed into simple sugars such as glucose, or fats (triglycerides) are hydrolyzed to give fatty acids and glycerol. Likewise, proteins are hydrolyzed to give amino acids. Cellular respiration is the process of oxidizing these hydrolyzed molecules to carbon dioxide to generate ATP. For instance, up to 36 molecules of ATP can be produced from a single molecule of glucose. Lodish, H. et al (2004) Molecular Cell Biology, 5th Ed. New York: WH Freeman. The three main pathways to generate energy in eukaryotic organisms are: glycolysis, the Krebs Cycle (also known as the citric acid cycle), and oxidative phosphorylation.

The main source of energy for living organisms is glucose. In breaking down glucose, the energy in the glucose molecule's chemical bonds is released and can be harnessed by the cell to form ATP molecules. The process by which this occurs consists of several stages. The first is called glycolysis (the prefix glyco refers to glucose, and lysis means to split), in which the glucose molecule is broken down into two smaller molecules called pyruvic acid. As further discussed below, the next stages are different for anaerobes and aerobes.

In glycolysis, glucose and glycerol are metabolized to pyruvate via the glycolytic pathway. In most organisms, glycolysis occurs in the cytosol. During this process, two ATP molecules are generated. Two molecules of NADH are also produced, which can be further oxidized via the electron transport chain and result in the generation of additional ATP molecules.

Glycolysis is the first stage in the release of energy from the glucose molecule. It occurs in the cytoplasm via many enzymes. Both aerobic and anaerobic organisms use glycolysis to break down glucose to pyruvate initially. After this stage, however, aerobic organisms utilize oxygen to obtain additional energy.

Figure 2:
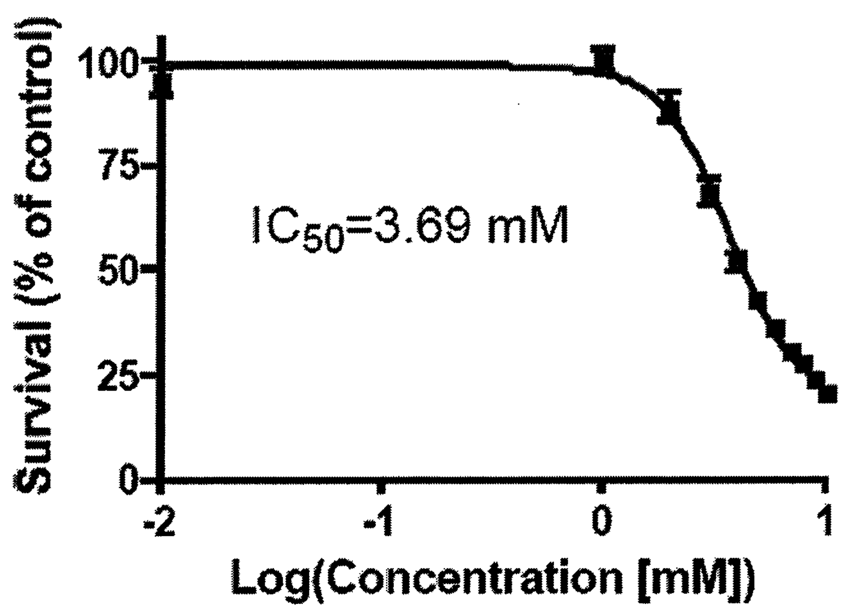
FIG. 2 shows in vitro activity of the compound of Example 2 in U87 glioblastoma cell line.
Figure 3:
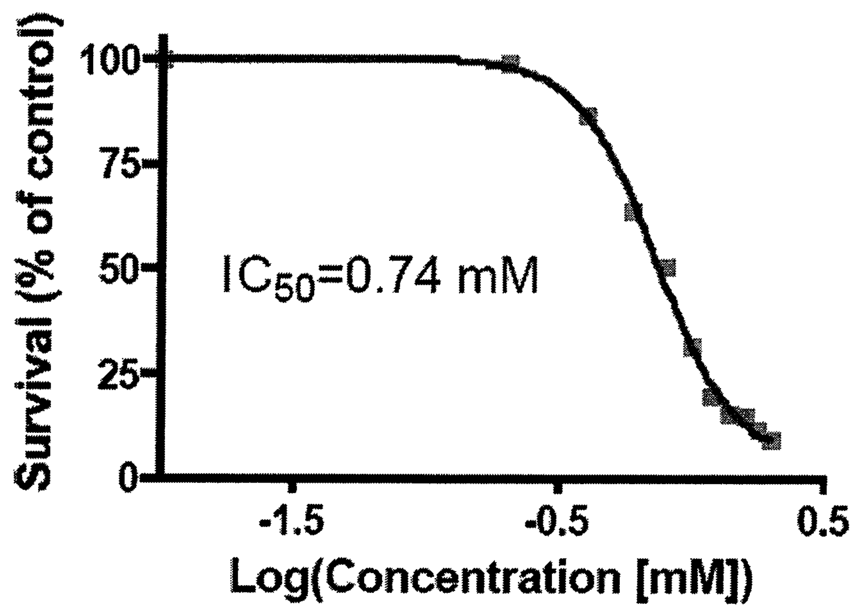
FIG. 3 shows in vitro activity of the compound of Example 5 in U87 glioblastoma cell line.
Figure 4:
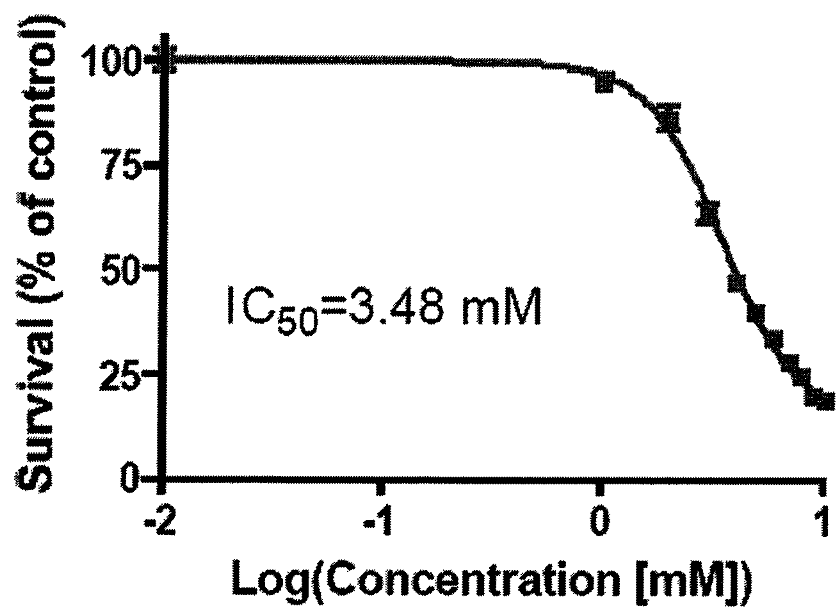
FIG. 4 shows in vitro activity of the compound of Example 3 in U87 glioblastoma cell line.
Figure 5:
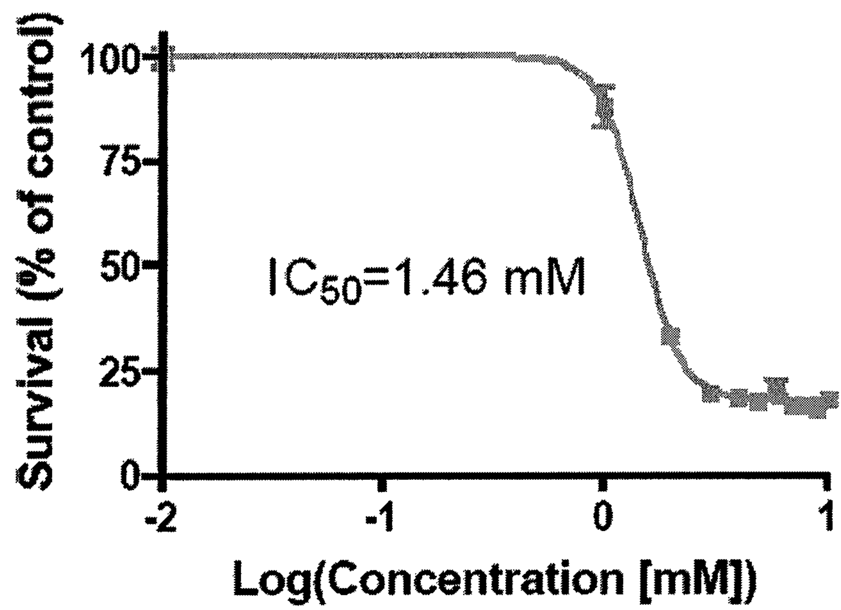
FIG. 5 shows in vitro activity of the compound of Example 4 in U87 glioblastoma cell line.
Figure 6:
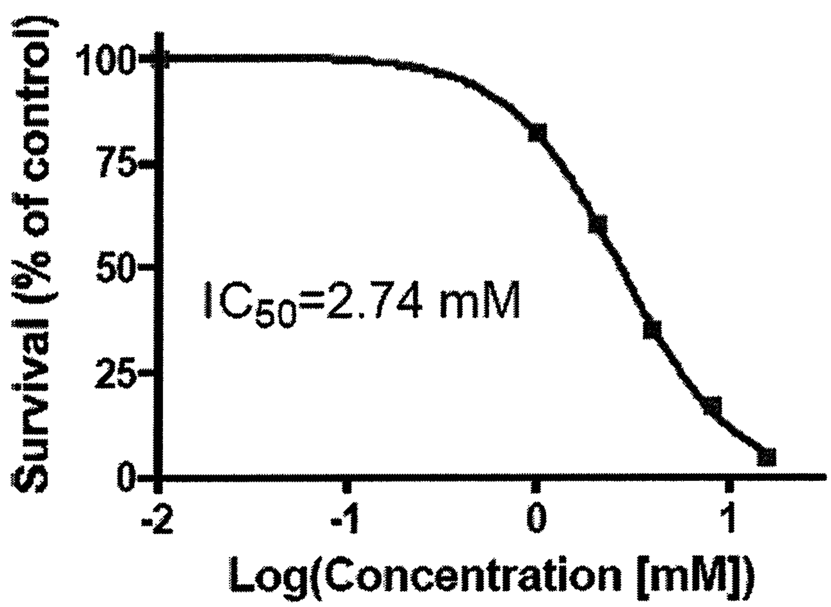
FIG. 6 shows in vitro activity of 2-DG in U87 glioblastoma cell line.

Glycolysis involves the breaking down of glucose into two smaller molecules of pyruvic acid, each pyruvic acid molecule having three carbon atoms, or half of the carbons in a glucose molecule. Noteworthy, for glycolysis to occur, two ATP molecules are necessary. As shown in FIG. 2, the first ATP molecule releases a phosphate group which then joins to the glucose molecule to form glucose phosphate. Then, the second ATP molecule contributes a phosphate group, forming a molecule called fructose diphosphate. The fructose diphosphate molecule splits into two molecules of glyceraldehyde phosphate "PGAL." Each PGAL molecule then releases electrons to a coenzyme NAD+ (nicotinamide adenine dinucleotide) and phosphate groups and energy to ADP.

As a result, two NAD+ molecules become NADH, and four molecules of ADP become ATP. In addition, the two molecules of PGAL have now become molecules of pyruvic acid, which has a molecular formula of $C_3H_4O_3$. Essentially, glycolysis requires an "investment" of two ATP molecules before it can begin. Since four ATP molecules are formed as products of the reaction, there is a net gain of two ATP molecules.

At this point in anaerobic organisms, pyruvic acid (pyruvate) undergoes additional processing in order to obtain additional energy. These processes, however, are significantly less efficient than the processes which aerobes utilize: the Krebs cycle and the electron transport chain. Glycolysis occurs in the cytoplasm and involves many enzyme-catalyzed steps that break down glucose (and other monosaccharides) into 2 pyruvate molecules. In return, the pathway leads to the generation of a sum of 2 ATP molecules. The pyruvate molecules generated from the glycolytic pathway enter the mitochondria from the cytosol. The molecules are then converted to acetyl co-enzyme A (Acetyl-CoA) for entry into the Krebs cycle. The Krebs cycle consists of the bonding of acetyl coenzyme-A with oxaloacetate to form citrate. The formed citrate is then broken down through a series of enzyme-catalyzed steps to generate additional ATP molecules.

In addition to generating ATP, the catabolic processes in glycolysis and the Krebs cycle also generate electrons that become stored in the form of reduced co-enzymes, such as NADH and FADH2. These co-enzymes participate in oxidative phosphorylation, where their electrons pass through an electron transport chain across the mitochondrial membrane. During this process, the protons from NADH and FADH2 enter the mitochondrial intermembrane space. Consequently, the electron transport chain leads to the formation of a proton gradient within the intermembrane space. Finally, the protons flux from the intermembrane space to the mitochondrial matrix through specific proton channels that catalyze the synthesis of additional ATP molecules.

Like normal cells, cancer cells also utilize metabolic pathways to generate ATP. However, classic observations by Otto Warburg show that highly proliferative tumors utilize glycolysis for cellular energy production rather than oxidative phosphorylation or the Krebs cycle, even in the presence of normoxia or adequate amounts of oxygen (termed oxidative glycolysis or the "Warburg effect"). *Energy Boost: The Warburg Effect Returns in a New Theory of Cancer, Journal of the National Cancer Institute*, Vol. 96, No. 24, Dec. 15, 2004 at 1806. *Hypoxia-inducible Factor* 1 *Activation by Aerobic Glycolysis Implicates the Warburg Effect in Carcinogenesis*, J. Bio. Chem. Vol. 277, No. 26, 23111 (2002). Under such conditions, the tumor cells up-regulate the expression of both glucose transporters and glycolytic enzymes, in turn, favoring an increased uptake of glucose (as well as their analogs) as compared to normal cells in an aerobic environment. This tumor adaptive response appears to hold true for malignant gliomas as well.

Other prevalent changes that occur with the progression of malignant tumors is the activation of the PI-3K/AKT pathway (typically by PTEN loss or through growth factor activity such as EGFR). This survival pathway activates a number of adaptive changes that include a stimulus for angiogenesis, inhibition of apoptosis, and metabolic shifts that promote activation of glycolysis and an increase in glucose uptake. Additionally, the malignant phenotype that up-regulates the glycolysis pathways are also induced by c-Myc, Hif-1α and STAT-3, all of which have been implicated in high-grade malignant transformation.

The aforementioned malignant transformations display a differential growth pattern. Namely, malignant tumors can grow in predominately hypoxic and mixed regions of variable degrees of normoxia. Relative hypoxic areas can be seen both in the center of the rapidly growing tumor mass, which often has regions of necrosis associated with this, as well as some relatively hypoxic regions within infiltrative components of the tumor as well. Accordingly, some of these relatively hypoxic regions may have cells that are cycling at a slower rate and may therefore be more resistant to many chemotherapy agents. For instance, gliomas can grow in a predominately infiltrative fashion with little to no contrast enhancement seen on MRI scans versus more rapidly growing contrast enhancing mass lesions.

Malignant gliomas as an example as well asmany other high-grade tumors are intrinsically resistant to conventional therapies. For instance, high-grade malignant tumors are highly angiogenic. In particular, most high-grade malignant tumors express large amounts of vascular endothelial growth factor (VEGF). AVASTIN®, a humanized monoclonal antibody against VEGF, has been used in combination with Irinotecan to treat patients with high grade gliomas. Results indicate very high response rates in over 60% of the treated patients (Society of Neuro-Oncology, 2005). This high response rate, however, is not translating into improved six-month progression-free survival or overall survival at this point. Furthermore, many patients treated with AVASTIN® displayed markedly worsening non-contrasting infiltrative tumor disease progression, indicating "tumor escape", or a shift of the growth phenotype to a predominately hypoxic pattern. (Conrad, C. A., et al., 2008 submitted).

Furthermore, many cancers such as malignant gliomas and pancreatic cancer are intrinsically resistant to conventional therapies and represent significant therapeutic challenges. Malignant gliomas have an annual incidence of 6.4 cases per 100,000 (Central Brain Tumor Registry of the United States, 2002-2003) and are the most common subtype of primary brain tumors and the deadliest human cancers. In its most aggressive manifestation, glioblastoma multiforme (GBM), the median survival duration for patients ranges from 12 to 14 months, despite maximum treatment efforts. In fact, approximately one-third of patients with GBM their tumors will continue to grow despite treatment with radiation and chemotherapy. Similarly, depending on the extent of the tumour at the time of diagnosis, the prognosis for pancreatic cancer is generally regarded as poor, with few victims still alive 5 years after diagnosis, and complete remission rare.

Further, in addition to the development of tumor resistance to treatments, another problem in treating malignant tumors is the toxicity of the treatment to normal tissues unaffected by disease. Often chemotherapy is targeted at killing rapidly-dividing cells regardless of whether those cells are normal or malignant. However, widespread cell death and the associated side effects of cancer treatments may not be necessary for tumor suppression if the growth control pathways of tumors can be disabled. For example, one approach is the use of therapy sensitization, i.e. using low dose of a standard treatment in combination with a drug that specifically targets crucial processes in the tumor cell, increasing the effects of the other drug.

Accordingly, the glycolytic pathway has become a potential target for the selective inhibition of many tumor cells, particularly glioblastomas and pancreatic cancers and other highly glycolytically sustained tumors. The inhibition of glycolysis would be selective for such tumor cells because normal cells in aerobic conditions would be able to survive such inhibition by generating energy through other pathways (e.g., the Krebs cycle, and oxidative phosphorylation). By contrast, when glycolysis is blocked in glycolytic tumor cells, the tumor cells would die because of an inability to utilize the aforementioned pathways.

However, current glycolytic inhibition approaches for cancer treatment present various challenges. For instance, many such treatments are not specific for the hypoxic environment of tumor cells. More importantly, current treatments are not selective inhibitors of glycolysis. Rather, such treatments can also target other pathways that are essential for normal cell function, such as glycosylation, where monosaccharides such as D-mannose are linked to proteins to form glycoproteins. Among other functions, glycoproteins are essential for maintaining the structural integrity of cell membrane Thus, interference with glycosylation can have clinical consequences. A need exists, therefore, for cancer treatments by the selective inhibition of glycolysis that do not substantially interfere with other metabolic pathways in the cell. Furthermore, there is currently an unmet need for the development of methods to treat cancer by molecules that demonstrate specificity for hypoxic cells. The present invention addresses these unmet needs.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, references to "glycolysis inhibitor," "glycolytic inhibitor" or "inhibitor(s) of glycolysis" are intended to refer to compounds or compositions that substantially inhibit or interfere with the activity of one or more enzymes involved in glycolysis.

As used herein, reference to "inhibition of glycolysis" is intended to refer to a decrease in glycolytic activity, a reduction in glycolytic activity, or the elimination of glycolytic activity.

As used herein, reference to "$IC_{50}$" is intended to refer to the concentration of a compound or composition that reduces the viability of cells to half the original level. In broader terms, $IC_{50}$ can refer to half the maximal inhibitory concentration of a substance for inhibiting various biological processes.

As used herein, reference to "therapeutically effective" is intended to qualify the amount of active ingredients that is used in the treatment of a disease or disorder described in the present disclosure. This amount will achieve the goal of reducing or eliminating the said disease or disorder.

As used herein, reference to "treatment" of a patient is intended to refer to procedures or applications of the methods of the present invention to a patient in order to temporarily or permanently cure, reduce, mitigate, or ameliorate a condition or disorder described in the present disclosure.

As used herein, reference to "patient" is intended to refer to all mammals including but not limited to humans, cows, dogs, cats, goats, sheep, pigs, and rabbits. Preferably, the patient is a human.

As used herein, reference to "hypoxic" is intended to refer to a condition characterized by low oxygen supply.

As used herein, reference to "normoxic" is intended to refer to a condition characterized by adequate oxygen supply.

As used herein, reference to "2-DG" in intended to refer to 2-deoxy-glucose.

Without being bound by theory, it is envisioned that the compounds presented herein may exert the effects by eliciting autophagy in addition to, or in lieu of apoptosis. Autophagy is a regulated process in which portions of the cytoplasm are first sequestered with double-membrane vesicles known as autophagosomes. Klionsky, D. J., et al., *Autophagy as a Regulated Pathway of Cellular Degradation, Science,* 2000, 290: 1717-1721. These autophagosomes then fuse with lysosomes to become autolysosomes or degradative autophagic vacuoles, after which the sequestered contents are degraded by lysosomal hydrolases. Autophagy leads to the extensive degradation of organelles, including mitochondria, which precedes nuclear destruction.

Autophagy is induced in various cell conditions; for example, it is responsible for the degradation of normal proteins in response to nutrient deprivation, differentiation, aging, transformation, and cancer. Cuervo, A. M., *Autophagy: In Sickness and in Health*, Trends Cell Biol, 2004, 14: 70-77; Shintani, T., et al., *Autophagy in Health and Disease: A Double-Edged Sword*, Science, 2004, 306: 990-995. In cancer research, autophagy is a novel concept, and its role remains unclear. In general, cancer cells show less autophagic degradation than normal cells. Bursch, W., et al., *Programmed Cell Death* (*PCD*). *Apoptosis, Autophagic PCD, or Others*? Ann. N.Y. Acad. Sci., 2000, 926: 1-12; Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906. Indeed, Beclin1, a mammalian homologue of yeast autophagy-related gene Atg6, plays a role of a tumor suppressor. Liang, X. H., et al., *Induction of Autophagy and Inhibition of Tumorigenesis by Beclin* 1, Nature, 1999, 402: 672-676; Qu, X., et al., *Promotion of Tumorigenesis by Heterozygous Disruption of the Beclin* 1 *Autophagy Gene*, J Clin Invest, 2003, 112:1809-1820; Yue. Z., et al., *Beclin* 1, *an Autophagy Gene Essential For Early Embryonic Development, Is a Haploinsufficient Tumor Suppressor*, Proc Natl Acad Sci USA, 2003, 100: 15077-15082.

In contrast, numerous cancer treatments have been shown to induce autophagy in established cancer cell lines. Altan, N., et al., *Defective Acidification in Human Breast Tumor Cells and Implications for Chemotherapy*, J Exp Med, 1998, 187: 1583-1598; Paglin, S., et al., *A Novel Response of Cancer Cells to Radiation Involves Autophagy and Formation of Acidic Vesicles, Cancer Res,* 2001, 61: 439-444; Kanzawa, T., et al., *Induction of Autophagic Cell Death in Malignant Glioma Cells by Arsenic Trioxide*, Cancer Res, 2003, 63: 2103-2108; Daido, S., et al., *Inhibition of the DNA-Dependent Protein Kinase Catalytic Subunit Radiosensitizes Malignant Glioma Cells by Inducing Autophagy*, Cancer Res, 2005, 65:4368-4375; Takeuchi, H., et al., *Synergistic Augmentation of Rapamycin-Induced Autophagy in Malignant Glioma Cells by Phosphatidylinositol* 3-*Kinase/Protein Kinase B Inhibitors*, Cancer Res, 2005, 65:3336-3346. However, whether autophagy helps kill tumor cells or instead protects them from the treatments' cell-damaging effect is still debated. Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906; Edinger, A. L., et al. *Defective Autophagy Leads to Cancer*, Cancer Cell, 2003, 4:422-424; Kondo, Y., et al., *Role of Autophagy in Cancer Development and Response to Therapy*, Nat Rev Cancer, 2005, 5:726-734; Hait, W. N., et al., *A Matter of Life or Death* (*or Both*): *Understanding Autophagy in Cancer*, Clin Cancer Res., 2006 Apr. 1, 12(7 Pt 1):1961-5.

Currently, methods to detect or quantify autophagy are somewhat limited. Demonstration of autophagic vacuoles on electron microscopy is an important standard; however, this analysis requires considerable skill and is neither easy nor quick. Other assays such as acridine orange or monodansyl cadaverine staining are not specific to autophagy. Paglin, S., et al., *A Novel Response of Cancer Cells to Radiation Involves Autophagy and Formation of Acidic Vesicles*, Cancer Res, 2001, 61: 439-444; Munafo, D. B., et al., *A Novel Assay to Study Autophagy: Regulation of Autophagosome Vacuole Size by Amino Acid Deprivation*, J Cell Sci, 2001, 114:3619-29. The use of the green-fluorescent protein (GFP)-tagged-rat microtubule-associated protein 1 light chain 3 (LC3) expression vector makes autophagy detection specific and easy, but this assay requires gene transfection and is not available for xenograft models or surgical specimens obtained from cancer patients. Kabeya, Y., et al., *LC*3, *a Mammalian Homologue of Yeast Apg*8*p, Is Localized in Autophagosome Membranes After Processing, EMBO J,* 2000, 19:5720-5728; Mizushima, N., et al., *Dissection of Autophagosome Formation Using Apg*5-*Deficient Mouse Embryonic Stem Cells*, J Cell Biol, 2001, 152:657-668.

Furthermore, the compounds and methods that are described herein can be used to prevent or treat Central Nervous System ("CNS") diseases and conditions such as CNS inflammatory and conditions, e.g., multiple sclerosis and progressive multi-focal leukoencephalopathy.

Moreover, the compounds and methods that are described herein can be used to prevent or treat inflammatory diseases and conditions, such as osteoarthritis, Rheumatoid arthritis, Crohn's disease, ulcerative colitis, and auto-immune diseases such as lupus and mixed auto-immune disease.

Diseases and conditions hemangioblastoma and polycythemia vera may also be advantageously prevented or treated with the compounds and methods described herein.

These compounds and methods can affect stem cell survival and differentiation by maintaining stem cell sternness, e.g., preventing the differentiation of stem cells.

The compounds taught herein may also be used for the reduction of multiple auto-immune diseases.

The compounds taught herein may also be used for the treatment of seizures, status epilepticus or epilepticus partialis continua.

The compounds presented herein to treat cancer may be administered in combination with one or more compounds and/or other agents including but not limited to anti-cancer agents, anti-angiogenic agents and/or autophagy inducing agents.

Anti-Cancer Agents

Anti-cancer agents that are suitable for use in the methods described herein include: antitumor antibiotics (anthracyclines, mitoxantrone, bleomycin, mithramycin); Fludarabine, Gemcetobine, temozolamide (Temodar); cyclophosphamides; fluoropyrimidines (such as capecitabine); fluorouracil (5-FU or Adrucil); nitrosoureas, such as procarbazine (Matulane), lomustine, CCNU (CeeBU), 3-[(4-amino-2-methyl-pyrimidin-5-yl)methyl]-1-(2-chloroethyl)-1-nitroso-urea carmustine (ACNU), (BCNU, BiCNU, Gliadel Wafer), and estramustine (Emcyt); nitrogen mustard; melphalan; chlorambucil; busulphan; ifosfamide nitrosoureas; thiotepa; antimitotic agents such as vinca alkaloids (e.g., vincristine) and taxoids (e.g., Taxol (paclitaxel)), Taxotere (docetaxel), epothilone analogs, discodermolide analogs, and eleutherobin analogs (e.g., ifosfamide, melphalan, chlorambucil, thiotepa, cisplatin, and carboplatin).

Temodar and other suitable anti-cancer agents may be administered at therapeutically effective dosages under different schedules, as envisioned by people of ordinary skill in the art. For instance, the anti-cancer agents can be administered at 100 mg per $m^2$ body weight for seven consecutive days on a bi-weekly basis. The anti-cancer agents may also be administered at the same dosage for 21 days on and 7 days off. Other therapeutic dosages and administration schedules can also be envisioned by people of ordinary skill in the art.

Anti-Angiogenic Agents

The anti-angiogenic agents useful in the disclosed methods include VEGF inhibitors (e.g., Avastin), VEGF Trap, Sorafinib, Sutin, linomide inhibitors of integrin-$\alpha\beta3$ function, angiostatin, razoxane, and the like.

Such anti-angiogenic agents may be small molecules, antibodies, aptamers, proteins, polypeptides, and other compounds or compositions that reduce or eliminate angiogenic activity. Anti-angiogenic agents may be administered at a therapeutically effective dose under different schedules. As an example, Avastin may be administered to a patient at a dose of 5, 10 or 15 mg per kg body weight once every two or three weeks. Alternatively, 3-20 mg/kg once every 2-3 weeks is suitable.

Autophagy-Inducing Agents

One or more autophagy-inducing agents may also be used in the methods presented herein. For instance, Rapamycin is useful as an autophagy-inducing agent. Other autophagy-inducing agents include concanavalin A, inhibitors of eEF-2 Kinase Inhibitors and histone deactylase inhibitors like SAHA.

The basis for adding one or more autophagy inducing agents to the combination therapies of the present invention is that our results indicate that sugar-based inhibitors of glycolysis kill tumor cells through this process. Autophagy is a regulated process in which portions of the cytoplasm are first sequestered with double-membrane vesicles known as autophagosomes. Klionsky, D. J., et al., *Autophagy as a Regulated Pathway of Cellular Degradation*, Science, 2000, 290: 1717-1721. These autophagosomes then fuse with lysosomes to become autolysosomes or degradative autophagic vacuoles, after which the sequestered contents are degraded by lysosomal hydrolases. Autophagy leads to the extensive degradation of organelles, including mitochondria, which precedes nuclear destruction.

Autophagy is induced in various cell conditions; for example, it is responsible for the degradation of normal proteins in response to nutrient deprivation, differentiation, aging, transformation, and cancer. Cuervo, A. M., *Autophagy: In Sickness and in Health*, Trends Cell Biol, 2004, 14: 70-77; Shintani, T., et al., *Autophagy in Health and Disease: A Double-Edged Sword*, Science, 2004, 306: 990-995. In cancer research, autophagy is a novel concept, and its role remains unclear. In general, cancer cells show less autophagic degradation than normal cells. Bursch, W., et al., *Programmed Cell Death (PCD). Apoptosis, Autophagic PCD, or Others*? Ann. N.Y. Acad. Sci., 2000, 926: 1-12; Ogier-Denis, E., et al., *Autophagy: A Barrier or an Adaptive Response to Cancer*, Biochim Biophys Acta, 2003, 1603: 113-128; Gozuacik, D., et al., *Autophagy as a Cell Death and Tumor Suppressor Mechanism*, Oncogene, 2004, 23: 2891-2906. Indeed, Beclin1, a mammalian homologue of yeast autophagy-related gene Atg6, plays a role of a tumor suppressor. Liang, X. H., et al., *Induction of Autophagy and Inhibition of Tumorigenesis by Beclin* 1, Nature, 1999, 402: 672-676; Qu, X., et al., *Promotion of Tumorigenesis by Heterozygous Disruption of the Beclin* 1 *Autophagy Gene*, J Clin Invest, 2003, 112:1809-1820; Yue. Z., et al., *Beclin* 1, *an Autophagy Gene Essential For Early Embryonic Development, Is a Haploinsufficient Tumor Suppressor*, Proc Natl Acad Sci USA, 2003, 100: 15077-15082.

The combination therapies of the present invention are particularly suitable for treating brain tumors including primary tumors such as glioblastoma or high-grade gliomas, and secondary brain tumors such as metastatic brain tumors. One unique property of the CNS is its striking predilection to uptake glucose and its analogs.

Hypoglycemic Agents

It is further envisioned that more optimal results will be obtained with the combination therapies if the patient is also treated with a therapeutically effective amount of one or more hypoglycemic agents under different schedules, preferably before treatment with compounds described herein. Hypoglycemic agents suitable for the present invention include compounds that reduce blood glucose levels. Non-limiting examples of such compounds include insulin, alpha-glucosidase inhibitors, sulfonylureas, meglitinides, D-phenylalanine derivatives, biguanides, thiazolidinediones, GLP-1 analogues, DPP-4 Inhibitors, and the like.

In addition to therapeutic modalities of these compounds, the fluorinated derivatives of these compounds (2-fluoro-monosaccarhides) either $F^{18}$ or $F^{19}$ substitutions can be used as diagnostic compound since the pharmokinetics and pharmocodynamics of these compounds may provide better characteristics than currently available compounds (i.e. 2-$F^{18}$DG)

with potentially better bioavailability and tumor uptake and retention. These attributes would not be obvious or predictable. Diagnostic superiority of these compounds represents a unique aspect of these compounds.

Modes of Administration

One of ordinary still in the art will readily recognize that the methods of treatment disclosed in the present invention can be accomplished through multiple routes of administration and with various quantities/concentrations of the compounds disclosed in the present invention. The preferred route of administration can vary depending on the compounds being used and such routes include, but are not limited to, oral, buccal, intramuscular (Lm.), intravenous (i.v.), intraparenteral (i.p.), topical, or any other FDA recognized route of administration. The administered or therapeutic concentrations will also vary depending upon the patient being treated and the compounds being administered.

The methods provided herein can be used in various forms of treatment. For instance, while it may be possible for the compounds to be administered as a raw chemical, it is also possible to present it as a pharmaceutical formulation. Accordingly, the patient invention can include a pharmaceutical formulation comprising the compound or a pharmaceutically acceptable salt, ester, prodrug or solvate thereof, together with one or more pharmaceutically acceptable carriers thereof and optionally one or more other therapeutic ingredients. The carrier(s) must be “acceptable” in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington’s Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association the compound (“active ingredient”) with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may also be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of DFGs to allow for the preparation of highly concentrated solutions.

It should be understood that in addition to the ingredients particularly mentioned above, the formulations of this invention may include other agents conventional in the art having regard to the type of formulation in question, for example those suitable for oral administration may include flavoring agents.

The amount of the compound that may be combined with the carrier materials to produce a single dosage form will vary depending upon the host treated and the particular mode of administration.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Besides being useful for human treatment, the compounds are also useful for veterinary treatment of companion animals, exotic animals and farm animals, including mammals, rodents, and the like. More preferred animals include horses, dogs, and cats.

In certain instances, it may be also be appropriate to administer compound in combination with another therapeutic agent. By way of example only, if one of the side effects experienced by a patient upon receiving one of compound herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of compounds described herein with another therapeutic agent (which also includes a therapeutic regimen) that also has therapeutic benefit. By way of example only, in a treatment for diabetes involving administration of one of compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the present invention) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Reference will now be made to specific examples illustrating the methods above. It is to be understood that the examples are provided to illustrate preferred embodiments and that no limitation to the scope of the invention is intended thereby.

General Synthetic Methods for Preparing Compounds

SYNTHESIS OF COMPOUND OF EXAMPLE 1

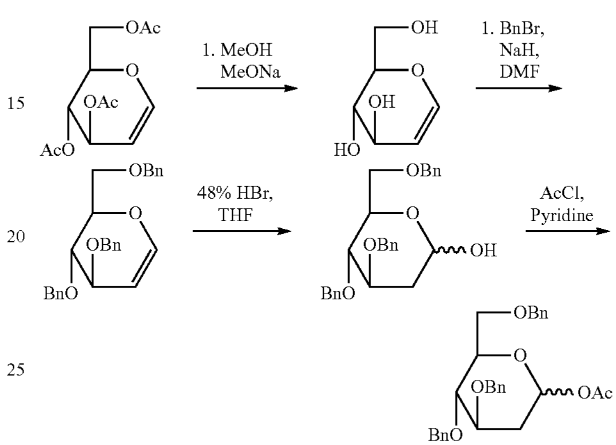

3,4,6-Tri-O-benzyl-D-glucal. Solution of glucal (1.46 g, 10 mmol) in DMF (15 mL) was prepared and cooled down to 0° C. Sodium hydride (60% suspension in mineral oil) (1.99 g, 50 mmol) was added and the mixture was stirred for 30 min. Benzyl bromide (6.85 g, 40 mmol) was added, the cooling bath was removed and the reaction mixture was stirred at room temperature until all substrate was converted into product. The mixture was cooled down to 0° C. (ice bath), and water (50 ml) was added slowly, followed by methylene chloride (30 mL). Organic layer was separated, water solution was extracted with methylene chloride (2×20 mL). Combined organic solutions were washed with water until neutral, then with brine, and dried over anhydrous sodium sulfate. Drying agents and solvents were removed and product was purified by column chromatography (SilicaGel 60 Merck), using hexanes; hexanes:ethyl acetate 40:1, 20:1 as eluents.

Fractions contained product were pooled together, evaporated to dryness and dried under reduced pressure to give 3.03 g of product. Yield 73%.

$^1$H NMR ($CDCl_3$, δ), ppm: 7.34-7.24 (m, 15 H, aromatic H), 6.43 (dd, 1H, J=6.1 Hz, J=1.1 Hz, H-1), 4.88 (dd, 1H, J=6.1 Hz, J=2.7 Hz, H-2), 4.84 (d, 1H, J=11.4 Hz, $CH_2Ph$), 4.67-4.54 (m, 1H, $CH_2Ph$), 4.22 (m, 1H, H-3), 4.07 (ddd, 1H, J=8.2 Hz, J=4.7 Hz, J=3.2 Hz, H-5), 3.87 (dd, 1H, J=6.2 Hz, J=8.6 Hz, H-4), 3.81 (dd, 1H, J=4.9 Hz, J=10.9 Hz, H-6), 3.76 (dd, 1H, J=3.1 Hz, J=10.7 Hz, H-6').

3,4,6-tri-O-benzyl-D-glucose. 47% Hydrobromic acid (0.5 mL) was added to a solution of 3,4,6-tri-O-benzyl-D-glucal (5 mmol) in tetrahydrofurane (50 mL), and obtained mixture was stirred in room temperature for 20 min. The reaction mixture was then poured into the 1% water solution of sodium bicarbonate (125 mL), and extracted with ethyl acetate (3×30 mL). Combined organic extracts were washed with water until neutral and dried over sodium sulfate. Drying agent and solvents were removed and product was purified by crystallization from ethyl acetrate/hexanes. Yield 76%, α:β ratio=3:1.

$^1$H NMR ($CDCl_3$, δ), ppm: 7.38-7.14 (m, 30H, aromatic Hα, β), 5.40 (m, 1H, H-1α), 4.89 (d, 1H, J=10.9 Hz, $CH_2Ph$ α), 4.88 (d, 1H, J=10.9 Hz, $CH_2Ph$ β), 4.77 (m, 1H, H-1β), 4.70-4.50 (m, 10H, $CH_2Ph$ α $CH_2Ph$ β) 4.08-4.00 (m, 2H, H-3α H-5α) 3.75-3.60 (m, 5H, H-6α H-6β, H-6'α H-6'β), 3.50 (m, 3H, H-4α, H-4β H-5β), 3.26 (d, 1H, J=6.3 Hz, OH β), 2.66 (m, 1H, OH α), 2.37 (ddd, 1H, J=12.5, Hz, J=5.1 Hz, J=2.2 Hz, H-2eβ) 2.29 (dd, 1H, J=12.9 Hz, J=5.0 Hz, H-2eα), 1.69 (dd, 1H, J=J=12.4 Hz, H-2aα), 1.57 (ddd, 1H, J=J=12.1 Hz, J=9.7 Hz. H-2aβ).

1-O-Acetyl-3,4,6 tri-O-benzyl-D-glucose.

Solution of 3,4,6-tri-O-benzyl-D-glucose (4.34 g, 10 mmol) in methylene chloride (30 mL) and pyridine (1.58 g, 1.62 mL, 20 mmol) was prepared and cooled down to 0° C. Acetyl chloride (11 mmol) was slowly added and the mixture was stirred in room temperature until all substrate disappeared (TLC). The reaction mixture was diluted with dichloromethane (50 mL), washed with water (2×30 mL) and dried over sodium sulfate. Drying agent and solvents were removed and product was purified by column chromatography (SilicaGel 60 Merck), using hexanes:ethyl acetate as eluents. Fractions contained product were pooled together, evaporated to dryness and dried under reduced pressure, to give 1-O-acetyl-3,4,6-tri-O-benzyl-D-glucose, Yield 65%, α:β ratio=3:1.

$^1$H NMR ($CDCl_3$, δ) ppm: 7.40-7.18 (m, 30H, H aromatic αβ, 6.28 (bs, 1H, H-1α), 5.71 (dd, 1H, J=10.0 Hz, J=2.2 Hz, H-1β) 4.94 (d, 1H, J=10.7 Hz, $CH_2Ph$ α), 4.91 (d, 1H, J=10.8 Hz, $CH_2Ph$ β), 4.74-4.52 (m, 10H, $CH_2Ph$ αβ), 3.99 (ddd, 1H, J=11.5 Hz, J=8.8 Hz, J=5.0 Hz, H-3α), 3.88 (ddd, 1H, J=9.8 Hz, J=3.2 Hz, J=1.8 Hz, H-5α), 3.85-3.63 (m, 7H, H-6αβ, H-6' αβ, H-4αβ H-3β, 3.55 (ddd, 1H, J=9.3 Hz, J=3.5 Hz, J=2.3 Hz, H-5 β), 240 (ddd, 1H, J=12.4 Hz, J=4.6 Hz, J=2.2 Hz, H-2eβ), 2.32 (ddd, 1H, J=13.6 Hz, J=5.0 Hz, J=1.5 Hz, H-2e α), 2.14 (s, 3H, $CH_3$β) 2.08 (s, 3H, $CH_3$α), 1.87 (ddd, 1H, J=13.6 Hz, J=11.5 Hz, J=3.5 Hz, 1H, H-2aα), 1.85-1.76 (m, 1H, H-2aβ).

1-O-Acetyl-2-deoxy-D-glucose (Compound of Example 1). Degussa 10% Pd/C (50% wet) (0.4 g) was added to the solution of 1-O-acyl-3,4,6-tri-O-benzyl-2-deoxy-D-glucose (5 mmol) in ethanol (50 mL). Obtained mixture was hydrogenated at room temperature using Paar apparatus with hydrogen (45 psi). After 12 hr reaction was completed, catalyst was filtered off and the solvent was evaporated to give a crude product. Product was purified by column chromatography (SilicaGel 60 Merck), using chloroform:methanol as eluent.

Fractions contained product were pooled together, evaporated to dryness and dried under reduced pressure to give the compound of Example 1. Yield 67%, α:β ratio=6.7:1, $[\alpha]^D$+ 107°, (c=1.02, methanol). spectra for α isomer, only few signal for β isomer can be resolved

SCHEME. SYNTHESIS OF COMPOUND OF EXAMPLE 2

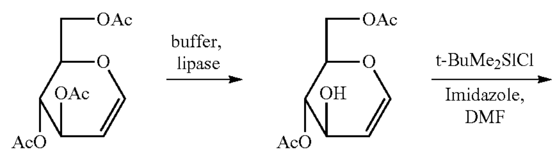

-continued

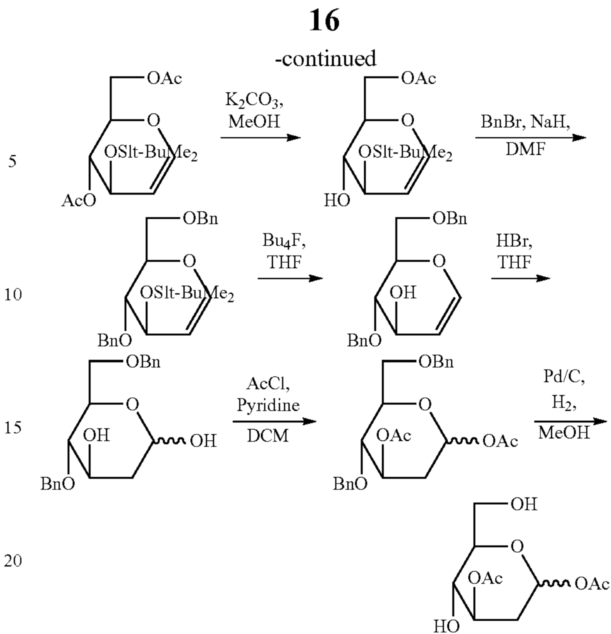

Synthesis of 4,6-di-O-acetyl-D-glucal. Per-O-acetyl glucal (27.5 mmol) was dissolved in phosphorane buffer (80 mL). Amano lipase (4.0 g) was added and the reaction mixture was stirred at room temperature for 24 hr. Brine (200 mL) was added and the obtained mixture was extracted with ethyl acetate (3×150 mL). Combined organic extracts were filtered trough Celite, and dried over anhydrous sodium sulfate. Drying agent and solvent were removed and product was purified by column chromatography (SilicaGel 60) using hexanes: ethyl acetate as eluents. 4,6-Di-O-Acetyl-D-glucal (26 mmol, yield 96%) was obtained.

$^1$HNMR ($CDCl_3$, δ) ppm: 6.42 (dd, 1H, J=6.1 Hz, J=1.5 Hz, H-1), 5.00 (1H, dd, J=6.3 Hz, J=9.1 Hz, H-4), 4.88 (dd, 1H, J=6.1 Hz, J=1.8 Hz, H-2), 4.43 (dd, J=5.4 Hz, J=12.3 Hz, H-6), 4.34 (m, 1H, H-3), 4.26 (dd, 1H, J=2.6 Hz, J=12.3 Hz, 1H, H-6'), 4.15 (ddd, 1 H, J=8.5 Hz, J=5.4 Hz, J=2.6 Hz, H-5), 2.57 (d, 1H, J=4 Hz, OH), 2.15 (s, 3H, $CH_3$), 2.11 (s, 3H, $CH_3$).

Synthesis of 4,6-di-O-acetyl-3-O-tert-butyldimethylsilyl-D-glucal. The mixture of 4,6-di-O-acetyl-D-glucal (8.7 mmol), t-butyldimethylsilyl chloride (10.4 mmol), imidazole (17.4 mmol) and DMF (20 mL) was prepared and stirred at room temperature for 2 hr. Water (40 mL) was added, and the mixture was extracted with hexanes (3×30 mL). Combined extracts were washed with water, and dried over anhydrous sodium sulfate. Drying agent and solvent were removed, and product was purified by column chromatography (SilicaGel 60) using hexanes:ethyl acetate as eluents. 4,6-Di-O-acetyl-3-O-tort-butyldimethylsilyl-D-glucal, (7.2 mmol, yield 83%) was obtained.

$^1$H NMR ($CDCl_3$, δ) ppm: 6.37 (dd, 1H, J=6.2 Hz, J=1.1 Hz, H-1), 5.08 (m, 1H, H-4), 4.88 (dd, 1H, J=6.2 Hz, J=2.1 Hz, H-2), 4.44 (ddd, 1H, J=1.8 Hz, J=4.7 Hz, J=12.3 Hz, H-6), 4.26-4.16 (m, 3H, H-3, H-5, H-6'), 2.11 (s, 3H, $CH_3$), 2.10 (s, 3H, $CH_3$), 0.90 (s, 9H, t-Bu), 0.11, 0.10 (2s, 3H ea., 2Me). $[\alpha]^{20}$−29.35 (c=1, chloroform).

Synthesis of 3-O-tert-butyldimethylsilyl-D-glucal. 3-O-(tert-butyldimethyl-silyl)-4,6-di-O-acetyl-D-glucal (11.9 g, 34.5 mmol) was dissolved in methanol (120 mL), then 1M solution of sodium methanolate in methanol (1 mL) was added. The reaction mixture was stirred in room temperature for 6 hours and 1M water solution of hydrochloric acid (1 mL) was added. Reaction mixture was evaporated to dryness and crude product was purified by column chromatography (SilicaGel 60 Merck), using hexanes:ethyl acetate as eluents to give 7.7 g of 3-O-(tert-butyldimethyl-silyl)-D-glucal, yield (85%), mp. 55.0-56.0° C.

$^{1}$H NMR ($CDCl_3$, δ) ppm: 6.33 (dd, 1H, J=6.1 Hz, J=1.5 Hz, H-1), 4.69 (dd, 1H, J=6.1 Hz, J=2.5 Hz, H-2), 4.26 (ddd, 1H, J=6.3 Hz, J=2.5 Hz, J=1.5 Hz, H-3), 3.97-3.90 (m, 3H, H-4, H-6, H-6'), 3.85-3.77 (m, 1H, H-5), 2.42 (d, 1H, J=4.2 Hz, OH), 2.26 (m, 1H, OH), 0.94 (s, 9H, t-Bu), 0.15 (s, 6H, $Me_2Si$). $[\alpha]^{20}$=−0.57 (c=1, chloroform).

Synthesis of 4,6-di-O-benzyl-3-O-tert-butyldimethylsilyl-D-glucal. 3-O-Tert-butyldimethylsilyl-D-glucal (4.8 mmol) was dissolved in DMF (50 mL). Sodium hydroxide (31 mmol), followed by tetrabutylammonium bromide (125 mg) and benzyl bromide (10.5 mmol) were added and the reaction mixture was stirred at room temperature for 16 hr. Solids were filtered off, brine (100 ml) was added, and obtained solution was extracted with hexanes (3×50 mL). Combined organic extracts were washed with water until neutral then dried over anhydrous sodium sulfate. Solids and solvents were removed and crude product was purified by column chromatography (SilicaGel 60) using hexanes:ethyl acetate as eluents. 4,6-Di-β-benzyl-3-O-tert-butyldimethylsilyl-D-glucal (3.0 mmol, yield 63%) was obtained.

$^{1}$H NMRR ($CDCl_3$, δ) ppm: 7.36-7.26 (m, 10H, Haromat.), 6.36 (dd, 1H, J=6.1 Hz, J=1.3 Hz, H-1), 4.84 (d, 1H, J=11.3 Hz, $CH_2Ph$), 4.68 (dd, 1H, J=6.1 Hz, J=2.8 Hz, H-2), 4.65 (d, 1H, J=11.3 Hz, $CH_2Ph$), 4.59 (s, 2H, $CH_2Ph$), 5.80 (ddd, 1H, J=5.8 Hz, J=2.7 Hz, J=1.2 Hz, H-3), 4.09 (ddd, 1H, J=8.2 Hz, J=5.5 Hz, J=2.7 Hz, H-5), 3.81 (dd, 1H, J=10.8 Hz, J=5.5 Hz, H-6), 3.72 (dd, 1H, J=10.8 Hz, J=2.6 Hz, H-6), 3.68 (dd, 1H, J=8.4 Hz, J=6 Hz, H-4), 0.92 (s, 9H, t-Bu), 0.11, 0.10 (2s, 3H ea, $Me_2$).

Synthesis of 4,6-di-O-benzyl-D-glucal. 4,6-Di-O-benzyl-3-O-tert-butyldimethylsilyl-D-glucal (3 mmol) was dissolved in THF (35 mL). Tetrabutyl fluoride (1M solution in THF) (3.5 mL) was added and the reaction mixture was stirred at room temperature overnight, then water (50 mL) was added and the mixture was extracted with ethyl acetate (3×50 mL). Combined organic extracts were washed with water until neutral, and dried over anhydrous sodium sulfate. Solids and solvents were removed and crude product was purified by column chromatography (SilicaGel 60) using hexanes:ethyl acetate as eluents. Pure 4,6-di-O-benzyl-D-glucal (2.61 mmol, yield 87%) was obtained. mp 53° C.

$^{1}$HNMR ($CDCl_3$, δ) ppm: 7.38-7.30 (m, 10H, Haromat.), 6.42 (dd, 1H, J=6 Hz, J=1.5 Hz, H-1), 4.82 (d, 1H, J=11.6 Hz, $CH_2Ph$), 4.77 (dd, 1 H, J=6.0 Hz, J=2.6 Hz, H-1), 4.72 (d, 1H, J=11.4 Hz, $CH_2Ph$), 4.67 (d, 1H, J=12 Hz, $CH_2Ph$), 4.60 (d, 1H, J=12 Hz, $CH_2Ph$), 4.36 (bs, 1H, H-3), 4.01 (ddd, 1H, J=10 Hz, J=J=3.3 Hz, H-5), 3.89-3.79 (m, 2H, H-6), 3.70 (dd, 1H, J=9.1 Hz, J=4.8 Hz, H-4).

Synthesis of 4,6-di-O-benzyl-2-deoxy-D-glucose. 4,6-di-O-benzyl-D-glucal (4.9 mmol) was dissolved in THF (60 mL). 48% Water solution of hydrobromic acid (0.4 mL) was added and the reaction mixture was stirred at room temperature. After reaction was completed, water (250 mL) was added, and pH of obtained solution was adjusted to 8 using saturated sodium carbonate. Water solution was then extracted with ethyl acetate (3×100 mL). Combined water extracts were washed with water until neutral, and dried over anhydrous sodium sulfate. Solids and solvents were removed and crude product was purified by column chromatography (SilicaGel 60) using hexanes:ethyl acetate as eluents. Pure 4,6-di-O-benzyl-2-deoxy-D-glucose (3.1 mmol, yield 63%) was obtained.

Synthesis of 1,3-di-O-acetyl-4,6-di-O-benzyl-2-deoxy-D-glucose (Compound of Example 2). 4,6-Di-O-benzyl-2-deoxy-D-glucose (3 mmol) was dissolved in dichloromethane (30 mL). Pyridine (18 mmol) was added, and the reaction mixture was cooled down to 0° C. Acetyl chloride (9 mmol) was added, and the reaction mixture was stirred at room temperature until reaction was completed, then reaction mixture was diluted with dichloromethane (70 mL), washed with water (3×50 mL) and dried over anhydrous sodium sulfate. Drying agent was filtered off, and solvent was evaporated. Toluene (50 mL) was added to the residue, and evaporated to dryness. Addition and evaporation of the toluene was repeated 3 times. Crude product was purified by column chromatography (SilicaGel 60) using hexanes:ethyl acetate as eluents, to give pure compound of Example 2, Yield 90% α:β ratio=1.7:1.

SYNTHESIS OF COMPOUND OF EXAMPLE 3

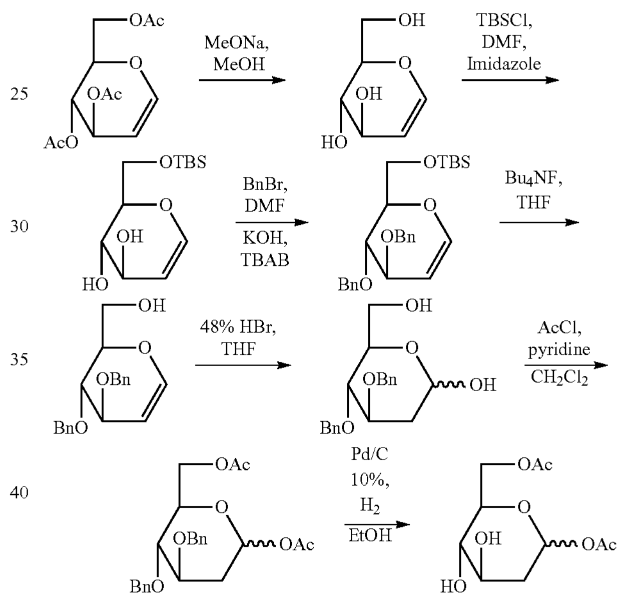

Synthesis of D-glucal. Potassium carbonate (50 g) was added to the solution of per-O-acetylated glucal (0.177 mol) in methanol (500 mL). The reaction mixture was stirred at room temperature overnight. Inorganic salts were filtered off, and filtrate was evaporated to dryness. Product was purified by column chromatography (SilicaGel 60) using chloroform:methanol as eluents, to give 0.159 mol of crystalline D-glucal (Yield 90%) (NMR spectra match that of literature).

Synthesis of 6-O-tert-butyldimethylsilyl-D-glucal. A solution of D-glucal (34 mmol) in DMF (50 mL) was prepared. Tert-butyldimethylsilyl chloride (37.4 mmol) followed by imidazole (68 mmol) was added and the reaction mixture was stirred at room temperature for 2 hr. Brine (250 mL) was added and obtained mixture was extracted with ethyl acetate (3×75 mL). Combined organic extracts were washed with water, and dried over anhydrous sodium sulfate. Solids and solvents were removed and product was separated by column chromatography (SilicaGel 60), using chloroform:methanol as eluents. 6-O-Tert-butyldimethylsilyl-D-glucal, (27.2 mmol, yield 80%) was obtained.

$^{1}$H NMR (DMSO-$d_6$, 300 MHz, δ) ppm: 6.28 (dd, 1H, J=6.0 Hz, J=1.5 Hz, H-1), 5.1 (d, 1H, J=5.6 Hz, OH), 4.86 (d, 1H, J=5.4 Hz, OH), 4.57 (dd, 1H, J=6 Hz, J=2.3 Hz, H-2), 3.96-3.90 (m, 1H, H-3), 3.88 (dd, 1H, J=11.4 Hz, J=2.3 Hz, H-6), 3.80 (dd, 1H, J=11.6 Hz, J=5.1 Hz, H-6), 3.61 (ddd, 1H, J=9.5 Hz, J=5.1 Hz, J=2.1 Hz, H-5), 3.38 (ddd, 1H, J=9.5 Hz, J=6.8 Hz, J=5.6 Hz, H-4), 0.87 (s, 9H, t-Bu), 0.04 (s, 6H, $Me_2$).

Synthesis of 3,4-di-O-benzyl-6-O-tert-butyldimethylsilyl-D-glucal. 6-O-tert-butyldimethylsilyl-D-glucal (11.5 mmol) was dissolved in dichloromethane (30 mL). Sodium hydroxide (23 mmol) followed by tetrabutylammonium bromide (5 mg) and benzyl bromide (27 mmol) were added and the reaction mixture was stirred at 40° C. After reaction was completed the reaction mixture was cooled down, solids were filtered off, filtrate was diluted with dichloromethane (100 mL), washed with water until neutral and dried over anhydrous sodium sulfate. Drying agent and solvents were removed and product was separated using column chromatography (SilicaGel 60) and hexanes:ethyl acetate as eluents. 3,4-di-O-benzyl-6-O-tert-butyldimethylsilyl-D-glucal (6.9 mmol, yield 60%) was obtained. $[\alpha]^D$−6.6 (c=1, chloroform).

$^1$H NMR ($CDCl_3$, 300 MHz, δ) ppm: 7.37-7.29 (m, 10H, Haromatic), 6.41 (dd, 1H, J=6.1 Hz, J=1.35 Hz, H-1), 4.88 (d, 1H, J=11.2 Hz, $CH_2Ph$), 4.86 (dd, 1H, J=6.1 Hz, J=2.6 Hz, H-2), 4.77 (d, 1H, J=11.2 Hz, $CH_2Ph$), 4.67, (d, 1H, J=11.7 Hz, $CH_2Ph$), 4.61 (d, 1H, J=11.7 Hz, $CH_2Ph$), 4.23 (ddd, 1H, J=6.8 Hz, J=2.6 Hz, J=1.5 Hz, H-3), 4.02-3.87 (m, 4H, H-4, H-5, H-6), 0.93 (s, 9H, t-Bu), 0.10, 0.09 (2s, 3H ea, $Me_2$).

Synthesis of 3,4-di-O-benzyl-D-glucal. Tetrabutylammonium fluoride (1M solution in THF) (5 mL) was added to the solution of 3,4-di-O-benzyl-6-O-tert-butyldimethylsilyl-D-glucal (4.5 mmol) in THF (50 mL). The reaction mixture was stirred at room temperature overnight, then brine (100 mL) was added. Obtained solution was extracted with ethyl acetate (3×50 mL). Combined organic extracts were washed with water until neutral, and dried over anhydrous sodium sulfate. Drying agent and solvent were removed and product was isolated using column chromatography (SilicaGel 60) and hexanes:ethyl acetate as eluents. 3,4-di-O-benzyl-Dglucal (3.51 mmol, yield 78%) was obtained.

$^1$H NMR ($CDCl_3$, 300 MHz, δ) ppm: 7.38-7.33 (m, 10H, Haromat.), 6.43 (dd, 1H, J=6.1 Hz, J=1.2 Hz, H-1), 4.92 (dd, 1H, J=6.1 Hz, J=2.7 Hz, H-2), 4.90 (d, 1H, J=11.5 Hz, $CH_2Ph$), 4.76 (d, 1H, J=11.5 Hz, $CH_2Ph$), 4.70 (d, 1H, J=11.6 Hz, $CH_2Ph$), 4.60 (d, 1H, J=11.6 Hz, CH2Ph), 4.27 (dddd, 1H, J=6.1 Hz, J=2.6 Hz, J=1.4 Hz, J=0.6 Hz, H-3), 3.98 (ddd, 1H, J=8.5 Hz, J=J=3.8 Hz, H-5), 3.89 (m, 2H, H-6), 3.84 (dd, 1H, J=8.5 Hz, J=6.2 Hz, H-4), 1.99 (bs, 1H, OH).

Synthesis of 3,4-di-O-benzyl-2-deoxy-D-glucose. 48% Hydrobromic acid (0.4 mL) was added to the solution of 3,4-di-O-benzyl-D-glucal (3.5 mmol) in THF (25 mL). The reaction mixture was stirred at room temperature for 30 min. Brine (50 mL) was added and pH of the obtained solution was adjusted to 8 with saturated sodium carbonate. Water solution was extracted with ethyl acetate (3×30 mL). Combined organic extracts were washed with water until neutral and dried over sodium sulfate. Drying agent and solvent were removed and product was separated by column chromatography (SilicaGel 60) using dichloromethane: methanol as eluents.

3,4-di-O-benzyl-2-deoxy-D-glucose (1.75 mmol, yield 50%) was obtained.

$^1$H NMR ($CDCl_3$, 300 MHz, δ) ppm: 7.39-7.30 (m, 10H, Haromat.), 5.38 (d, 1H, J=2.4 Hz, H-1α), 4.97 (d, 1H, J=11.0 Hz, $CH_2Ph$ α), 4.96 (d, 1H, J=11.0 Hz, $CH_2Ph$ β), 4.84 (d, 1H, J=8.4 Hz, H-1β), 4.74-4.62 (m, 3H, $CH_2Ph$ α and β), 4.09 (ddd, 1H, J=11.3 Hz, J=8.8 Hz, J=4.9 Hz, H-3α), 3.95 (ddd, 1H, J=9.6 Hz, J=4.8 Hz, J=2.8 Hz, H-5α), 3.90-3.81 (m, 2H, H-6 αβ, 3.76-3.66 (m, 2H, H-6 αβ), 3.49 (dd, 1H, J=J=9.6 Hz, H-4α), 3.48 (dd, 1H, J=J=9.2 Hz, H-1β), 3.88 (ddd, 1H, J=9.3 Hz, J=4.8 Hz, J=2.6 Hz, H-5β), 3.10 (bs, 1H, OH), 2.41 (ddd, 1H, J=12.6 Hz, J=5.0 Hz, J=1.9 Hz, H-2e, β), 2.32 (ddd, 1H, J=13.1 Hz, J=4.9 Hz, J=1.1 Hz, H-2e, α), 1.67 (ddd, 1H, J=13.1 Hz, J=11.5 Hz, J=4.5 Hz, H-2a, α), 1.58 (ddd, 1H, J=12.6 Hz, J=J=9.7 Hz, H-2a, β).

Synthesis of 1,6-di-O-acetyl-3,4-di-O-benzyl-2-deoxy-D-glucose. The mixture of 3,4-di-O-benzyl-2-deoxy-D-glucose (1.6 mmol) and pyridine (9.6 mmol) in dichloromethane (20 mL) was prepared and cooled down to 0° C. Acetyl chloride (4.8 mmol) was added and the reaction mixture was stirred at room temperature. After reaction was completed, the reaction mixture was diluted with dichloromethane (80 mL) and washed with water, then dried over anhydrous sodium sulfate. Drying agent and solvents were removed and product was separated using column chromatography (SilicaGel 60) with hexanes:ethyl acetate as eluents, go give pure 1,6-di-O-acetyl-3,4-di-O-benzyl-2-deoxy-D-glucose. Yield 75%, α:β ratio=1.3:1.

$^1$H NMR ($CDCl_3$, 300 MHz, δ) ppm: 7.38-7.28 (m, 10H, Haromat.), 6.24 (d, 1H, J=1.8 Hz, H-1α), 5.72 (dd, 1H, J=10.0 Hz, J=2.1 Hz, H-1β), 4.97 (d, 1H, J=10.8 Hz, $CH_2Ph$ α), 4.95 (d, 1H, J=10 Hz, $CH_2Ph$ β), 4.74-4.62 (m, 3H, $CH_2Ph$ α, β), 4.38-4.13 (m, 2H, H-6 α, β), 4.02 (ddd, 1H, J=11.4 Hz, J=8.8 Hz, J=5.0 Hz, H-3α), 3.93 (ddd, 1H, J=9.8 Hz, J=4.0 Hz, J=2.2 Hz, H-5α), 3.78 (ddd, 1H, J=11.4 Hz, J=8.4 Hz, J=5.1 Hz, H-3β), 3.61 (ddd. 1H, J=6.9 Hz. J=J=3.5 Hz, H-5β), 3.57 (dd, 1H, J=J=9.6 Hz, H-4-α), 3.52 (dd, 1H, J=J=9.6 Hz, H-4β), 2.41 (ddd, 1H, J=12.5 Hz, J=5.0 Hz, J=2.5 Hz, H-2e β), 2.33 (ddd, 1H, J=13.5 Hz, J=4.9 Hz, J=1.4 Hz, H-2e α), 2.09, 2.06 (2s, 3H ea, OAc).

Synthesis of 1,6-di-O-acetyl-3,4-di-O-benzyl-2-deoxy-D-glucose (Compound of Example 3). Pd/C (10%, containing 50% of water) (100 mg) was added to the solution of 1,6-di-O-acyl-3,4-di-O-benzyl-2-deoxy-D-glucose (1 mmol) in 95% anhydrous ethanol (100 mL). Obtained mixture was hydrogenated at room temperature using Paar apparatus with hydrogen (45 psi). After 24 hr reaction was completed, catalyst was filtered off through Celite, and the solvent was evaporated to give a crude product. Product was purified by column chromatography (SilicaGel 60 Merck), using chloroform: methanol as eluent. Fractions contained product were pooled together, evaporated to dryness and dried under reduced pressure.

SYNTHESIS OF COMPOUND OF EXAMPLE 4

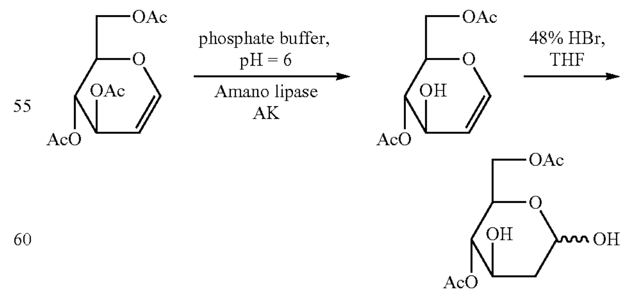

4,6-Di-O-acetyl-D-glucal. Mixture of peracetylated glucal (2.72 g, 10 mmol) in phosphorane buffer pH=7 (30 mL) and Amano lipase AK (1.8 g) was stirred at room temperature for 4 hours. Water (50 mL) followed by ethyl acetate (50 mL)

were added to the reaction mixture. Organic layer was separated, water solution was extracted with ethyl acetate (2×50 mL). Combined organic extracts were washed with water, filtered through Celite and dried over anhydrous sodium sulfate. Drying agent was filtered off, and solvent was evaporated to dryness Obtained crude product was purified by column chromatography (SilicaGel 60 Merck), using hexanes:ethyl acetate as an eluent to give 2.09 g of pure 4,6-di-O-acetyl-D-glucal (colorless oil). Yield (91%).

$^1$HNMR ($CDCl_3$, δ) ppm: 6.42 (dd, 1H, J=6.1 Hz, J=1.5 Hz, H-1), 5.00 (1H, dd, J=6.3 Hz, J=9.1 Hz, H-4), 4.88 (dd, 1H, J=6.1 Hz, J=1.8 Hz, H-2), 4.43 (dd, J=5.4 Hz, J=12.3 Hz, H-6), 4.34 (m, 1H, H-3), 4.26 (dd, 1H, J=2.6 Hz, J=12.3 Hz, 1H, H-6'), 4.15 (ddd, 1H, J=8.5 Hz, J=5.4 Hz, J=2.6 Hz, H-5), 2.57 (d, 1H, J=4 Hz, OH), 2.15 (s, 3H, $CH_3$), 2.11 (s, 3H, $CH_3$).

4,6-Di-O-acetyl-2-deoxy-D-glucose (Compound of Example 4). 48% Solution of hydrobromic acid (0.5 mL) was added to the mixture of 4,6-di-O-acetyl-D-glucal (0.506 g, 2.2 mmol) in tetrahydrofurane (20 mL). The mixture was stirred at room temperature for 30 min, then pH of the reaction mixture was adjusted to 8 by addition of saturated solution of sodium bicarbonate. Obtained solution was extracted with ethyl acetate (3×50 mL). Organic extracts were combined, washed with water until neutral, and dried over anhydrous sodium sulfate Drying agent and solvent were removed and product was purified by column chromatography (SilicaGel 60, Merck) using chloroform:methanol 100:1, 98:2 as eluents. Fractions contained pure product were evaporated to dryness to give 0.240 g of compound of Example 4 (yield 44%). (ddd, J=J=13.0 Hz, J=3.5 Hz, 1H, H-2aα), 1.41 (ddd, J=J=12.1 Hz, J=9.7 Hz, 1H, H-2aβ).

3,6-di-O-Acyl-2-deoxy-D-glucose

COMPOUND OF EXAMPLE 5

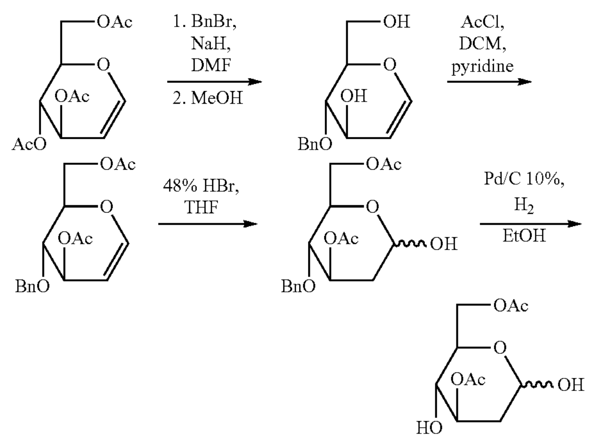

4-O-Benzyl-D-glucal. The suspension of NaH (1.9 mol) in DMF (650 mL) was prepared and cooled down to 0° C. Per-acetylated glucal (100 g, 0.36 mol) was added in small portions, and obtained mixture was stirred at 0° C. for 30 min., then benzyl bromide (50 mL, 0.42 mol) was added dropwise. The cooling bath was removed and stirring was continued until all substrate disappeared (TLC). After reaction was completed methanol (150 mL) was added slowly and the mixture was stirred for additional 30 min. Water (1 L) was added and solution was extracted with ethyl acetate (3×500 mL). Combined organic extracts were washed with water until neutral and dried over sodium sulfate. Drying agent and solvents were removed and product was separated by column chromatography (SilicaGel 60), using hexanes:ethyl acetate as eluents. Yield 72%, mp. 98.5-100.0° C.

$^1$H NMRR ($CDCl_3$, δ) ppm: 7.43-7.30 (m, 5H, H arom), 6.38 (dd, 1H, J=6.0 Hz, J=1.6 Hz, H-1), 4.87 (d, 1H, J=11.6 Hz, $CH_2Ph$), 4.82 (d, 1H, J=11.6 Hz, $CH_2Ph$), 4.76 (dd, 1H, J=6.0 Hz, J=2.5 Hz, H-2), 4.40 (bs, 1H, H-3), 3.99-3.86 (m, 3H, H-5, H-6a, H-6b), 3.65 (dd, 1H, J=9.0 Hz, J=6.8 Hz, H-4), 1.96 (bs, 1H, OH), 1.89 (bs, 1H, OH) Anal. Elem. Calc for: $C_{13}H_{16}O_4$C, 66.09; H, 6.83; Found: C, 66.00; H, 6.77; $[\alpha]^D$+10.4 (c=1.4, chloroform).

3,6-di-O-acyl-4-O-benzyl-D-glucal. Solution of 4-O-benzyl-D-glucal (10 mmol) in a mixture of methylene chloride (30 mL) and pyridine (40 mmol) was prepared, and cooled down to 0° C. Acyl chloride (22 mmol) was slowly added and the mixture was stirred at room temperature until all substrate disappeared (TLC). The reaction mixture was diluted with dichloromethane (50 mL) then washed with water (2×30 mL) and dried over anhydrous sodium sulfate. Drying agent and solvents were removed and product was purified by column chromatography (SilicaGel 60 Merck), using hexanes:ethyl acetate as eluents.

4-O-benzyl-3,6-di-O-acetyl-D-glucose. 48% Hydrobromic acid water solution (0.5 mL) was added to a mixture of 4-O-benzyl-3,6-di-O-acetyl-D-glucal (5 mmol) in tetrahydrofuran (50 mL), and obtained solution was stirred in room temperature. After reaction was completed (TLC) the reaction mixture was poured into the 10% water solution of sodium bicarbonate (125 mL), and water solution was extracted with ethyl acetate (3×30 mL). Combined organic extracts were washed with water and dried over sodium sulfate. Drying agent and solvents were removed and product was purified by column chromatography (SilicaGel 60 Merck), using hexanes:ethyl acetate as eluents.

Fractions contained product were pooled together, evaporated to dryness and dried under reduced pressure.

3,6-di-O-acetyl-D-glucose. Degussa 10% Pd/C (50% wet) (0.4 g) was added to the solution of 4-O-benzyl-3,6-di-O-acetyl-D-glucose (5 mmol) in ethanol (50 mL). Obtained mixture was hydrogenated at room temperature using Paar apparatus with hydrogen (45 psi) After 12 hr reaction was completed (TLC), catalyst was filtered off and the solvent was evaporated to give a crude product. Product was purified by column chromatography (SilicaGel 60 Merck), using hexanes:ethyl acetate as eluent.

Fractions contained product were pooled together, evaporated to dryness and dried under reduced pressure.

Synthesis of 6-O-acetyl-2-deoxy-D-glucose

COMPOUND OF EXAMPLE 6

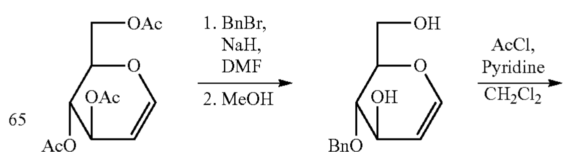

-continued

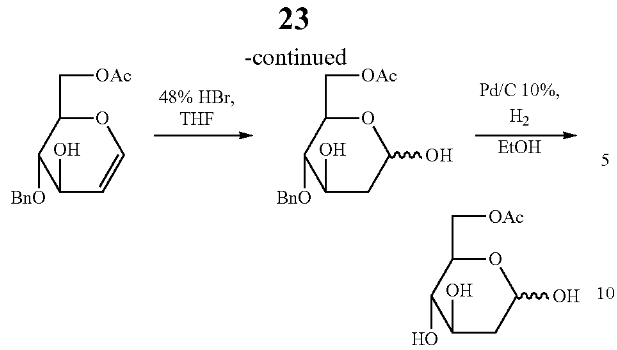

Synthesis of 6-O-acetyl-4-O-benzyl-D-glucal. 4-O-benzyl-D-glucal (21.2 mmol) and pyridine (45 mmol), were dissolved in dichloromethane (100 mL). Obtained solution was cooled down to 0° C., and acetyl chloride (25 mmol) was added. The mixture was stirred at 0° C. After reaction was completed, the reaction mixture was washed with water (3×50 mL), dried over anhydrous sodium sulfate. Drying agent and solvent were removed and product was purified by column chromatography (Silicagel 60) using hexanes:ethyl acetate as eluents. Yield 50%.

$^1$HNMR ($CDCl_3$, 300 MHz, δ) ppm: 7.39-7.33 (m, 5H, Haromat), 6.37 (dd, 1H, J=6 Hz, J=1.5 Hz, H-1), 4.86 (d, 1H, J=11.5 Hz, $CH_2Ph$), 4.78 (d, 1H, J=11.5 Hz, $CH_2Ph$), 4.77 (dd, 1H, J=6.8 Hz, J=4.3 Hz, H-2), 4.50 (dd, 1H, J=12.1 Hz, J=2.4 Hz, H-6), 4.43 (ddd, 1H, J=6.6 Hz, J=J=1.6 Hz, H-3), 4.35 (dd, 1H, J=12.1 Hz, J=5.2 Hz, H-6), 2.10 (s, 3H, OAc).

Synthesis of 6-O-acyl-4-O-benzyl-2-deoxy-D-glucose. 6-O-Acetyl-4-O-benzyl-D-glucal (2.5 mmol) was dissolved in THF (50 mL). 48% Water solution of hydrobromic acid (0.5 mL) was added and the reaction mixture was stirred at room temperature. After 1 hr, reaction was completed, water (250 mL) was added, then pH of obtained solution was adjusted to 8 using saturated sodium carbonate. Water solution was then extracted with ethyl acetate (3×100 mL). Combined water extracts were washed with water until neutral, and dried over anhydrous sodium sulfate. Solids and solvents were removed and crude product was purified by column chromatography (SilicaGel 60) using hexanes:ethyl acetate as eluents. (Yield 48%).

Synthesis of 6-O-acetyl-2-deoxy-D-glucose. Pd/C (10%, contained 50% of water) (40 mg) was added to the solution of 6-O-acetyl-4-O-benzyl-2-deoxy-D-glucose (1.15 mmol) in ethyl alcohol (50 mL). The mixture was hydrogenated using Paar apparatus (at 45 psi of $H_2$) for 24 hr. The reaction mixture was then filtered through Celite, evaporated to dryness, and product was purified by column chromatography (SilicaGel, 60) using chloroform:methanol as eluent. (Yield 48%).

The compounds as illustrated in the following examples were made.

EXAMPLE 1

1-O-Acetyl-2-deoxy-D-glucose

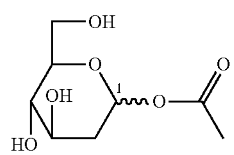

$^1$H NMR (DMSO-$d_6$, δ) ppm: 6.04 (d, 1H, J=2.2 Hz, H-1), 4.99 (d, 1H, J=5.4 Hz, OH), 4.89 (d, 1H, J=5.0 Hz, OH), 4.48 (dd, 1H, J=6.2 Hz, J=5.6 Hz, OH), 3.69-3.40 (m, 4H, H-3, H-5, H-6), 3.28 (ddd, 1H, J=J=9.3 Hz, J=5.3 Hz, H-4), 2.04 (s, 3H, OAc), 1.93 (ddd, 1H, J=13.6 Hz, J=4.9 Hz, J=1.3 Hz, H-2e), 1.58 (ddd, 1H, J=13.6 Hz, J=12.4 Hz, J=3.5 Hz, H-2a).

EXAMPLE 2

1,3-di-O-acetyl-4,6-di-O-benzyl-2-deoxy-D-glucose

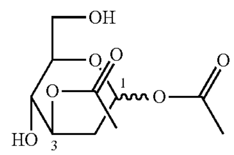

$^1$H NMRR ($CDCl_3$, 300 MHz, δ) ppm: 7.40-7.17 (m, 10H, Haromat.), 6.27 (s, 1H, J=1.1 Hz, H-1α), 5.78 (dd, 1H, J=10 Hz, J=2.3 Hz, H-1β), 5.32 (ddd, 1H, J=11.5 Hz, J=9.1 Hz, J=5.3 Hz, H-3α), 5.05 (ddd, 1H, J=11.1 Hz, J=9.0 Hz, J=5.1 Hz, H-3β), 4.72-4.50 (m, 4H, $CH_2$ α and β), 3.92 (ddd, 1H, J=9.6 Hz, J=J=2.2 Hz, H-5α), 3.86-3.76 (m, 4H, H-4β, H-6ab β, H-6a α), 3.76 (dd, 1H, J=J=9.3 Hz, H-4α), 3.68 (dd, 1H, J=10.8 Hz, J=2.0 Hz, H-6α), 3.58 (ddd, 1H, J=9.6 Hz, J=3.4 Hz, J=2.1 Hz, H-5β), 2.37 (ddd, 1H, J=12.2 Hz, J=5.2 Hz, J=2.2 Hz, H-2e β), 2.28 (ddd, 1H, J=13.4 Hz, J=5.3 Hz, J=1.6 Hz, H-2e α), 1.88 (ddd, 1H, J=13.4 Hz, J=11.5 Hz, J=3.7 Hz, H-2a α), 1.77 (ddd, 1H, J=11.9 Hz, J=J=J=10 Hz, H-2a β), 2.12, 2.11, 2.01, 2.00 (4s, 3H ea OAc).

EXAMPLE 3

1,6-di-O-acetyl-3,4-di-O-benzyl-2-deoxy-D-glucose

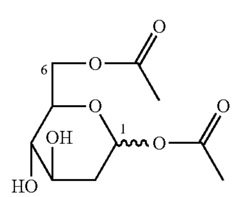

$^1$H NMR ($CDCl_3$, 300 MHz, δ) ppm: 6.25 (d, 1H, J=2.7 Hz, H-1α), 5.78 (dd, 1H, J=10.2 Hz, J=2.3 Hz, H-1β), 4.71 (dd, 1H, J=12.5 Hz, J=3.4 Hz, H-6α), 4.70 (dd, 1H, J=12.5 Hz, J=3.2 Hz, H-6β), 4.19 (dd, 1H, J=12.5 Hz, J=2.2 Hz, H-6β), 4.13 (dd, 1H, J=12.5 Hz, J=2.2 Hz, H-6α), 4.02 (ddd, 1H, J=11.4 Hz, J=9.1 Hz, J=5 Hz, H-3α), 3.82-3.64 (m, 2H, H-3p, H-5α), 3.47 (ddd, 1H, J=9.6 Hz, J=3.3 Hz, J=2.2 Hz, H-5β), 3.40 (bs, 1H, OH), 3.27 (dd, 1H, J=J=9.5 Hz, H-4α), 3.22 (dd, 1H, J=J=9.5 Hz, H-4β), 2.63 (bs, 1H, OH), 2.20 (ddd, 1H, J=13.7 Hz, J=5.1 Hz, J=1.6 Hz, H-2e α), 2.18 (s, 6H, OAc), 2.14, 2.11 (2s, 3H ea, OAc), 1.83 (ddd, 1H, J=13.6 Hz, J=11.7 Hz, J=3.6 Hz, H-2a α), 1.75 (ddd, 1H, J=J=10.0 Hz, J=12.1 Hz, H-2a β).

EXAMPLE 4

4,6-Di-O-acetyl-2-deoxy-D-glucose

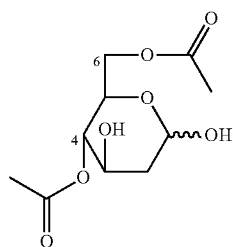

α/β ratio 5:3; $^1$H NMR (DMSO-d6+$D_2O$, δ) 5.17 (dd, J=2.1 Hz, 1H, H-1α), 4.72 (dd, J=9.5 Hz, J=1.7Hz, 1H, H-1β), 4.55 (dd, J=J=9.5 Hz, 1H, H-4α), 4.48 (dd. J=J=9.7 Hz, 1H, H-4β), 4.08-4.00 (m, 2H, H-6α H-6β) 3.95-3.88 (m, 2H, H-6'α H-6'β, H-5α) 3.86 (ddd, J=11.9 Hz, J=9.4 Hz, J=5.3 Hz, 1H, H-3α), (ddd, J=11.8 Hz, J=9.0 Hz, J=5.0 Hz, 1H, H-3β), (ddd, J=9.6 Hz, J=5.4 Hz, J=2.3 Hz, 1H, H-5β), 2.02 (s, 3H, OAc α) 2.01 (s, 3H, OAc β) 2.00 (m, 1H, H-2eβ) 1.99 (s, 3H, OAc α), 1.98 (s, 3H, OAc β), 1.90 (ddd, J=12.8 Hz, J=5.2 Hz, J=0.9 Hz, 1H, H-2eα), 1.55.

EXAMPLE 5

3,6-di-O-acetyl-D-glucose

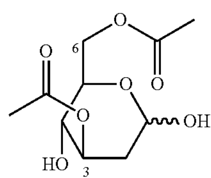 [SMILES: CC(=O)OCC1OC(O)CC(OC(C)=O)C1O]

EXAMPLE 6

6-O-acetyl-2-deoxy-D-glucose

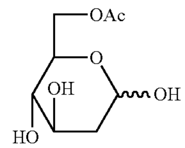

$^1$HNMR ($CDCl_3$, 300 MHz δ) ppm: 7.39-7.33 (m, 5H, Haromat), 5.39 (bs, 1H, H-1), 4.8-4.7 (m, 5H, H-113, $CH_2Ph$ αβ), 4.45 (dd, 1H, J=11.9 Hz, J=2.2 Hz, H-6β), 4.42 (dd, 1H, J=9.7 Hz, J=2.2 Hz, H-6 β), 4.60 (dd, 1H, J=12.0 Hz, j=1.6 Hz, H-6 α), 4.27-4.10 (m, 2H, H-3α, H-6β), 4.06 (ddd, 1H, J=9.9 Hz, J=4.7 Hz, J=2.1 Hz, H-5α), 3.83-3.77 (m, 1H, H-3β), 3.52 (ddd, 1H, J=9.5 Hz, J=5.1 HZ, J=2.3 Hz, H-5β), 3.47 (d, 1H, J=6.2 Hz, OHβ), 3.34 (dd, 1H, J=9.7 Hz, J=9.0 Hz, H-4α), 3.32 (dd, 1H, J=8.5 Hz, J=9.6 Hz, H-4β), 2.83 (dd, 1H, J=2.9 Hz, J=2.2 Hz, OHα), 2.29 (ddd, 1H, J=13.9 HZ, J=5.3 Hz, J=1.9 Hz, H-2eβ), 2.18 (ddd, 1H, J=13.0 Hz, J=5.1 Hz, J=1.2 Hz, H-2eα), 2.13 (s, 6H, OAc), 1.71 (ddd, 1H, J=13.5 Hz, J=3.5 Hz, J=2.0 Hz, H-2aα), 1.62 (ddd, 1H, J=12.6 Hz, J=9.4 Hz, J=11.7 Hz, H-2aβ).

Additional novel compounds useful in the methods described herein include:

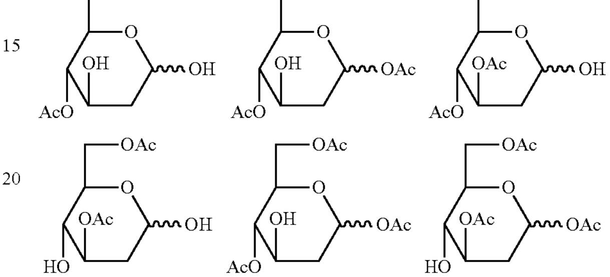

Other compounds useful in the methods described herein include:

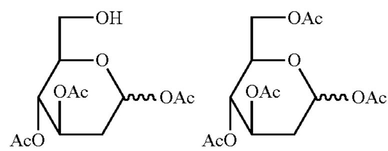

In Vitro Activity

In vitro activity in pancreatic Colo357-FG cell line is provided below in Table 1.

TABLE 1

| Compound | Structure | $IC_{50}$ [mM] Colo357FG |
|---|---|---|
| 2-DG | $CH_2OH$ O OH OH HO | 9.7 |
| Example 5 | $CH_2OAc$ O OAc OH HO | 1.6 |
| Example 1 | OH O OH OAc HO | 11.9 |

TABLE 1-continued

| Compound | Structure | $IC_{50}$ [mM] Colo357FG |
|---|---|---|
| Example 2 | OH, O, OAc, OAc, HO | 15.8 |
| Example 3 | OAc, O, OH, OAc, HO | 17.2 |
| Example 4 | OAc, O, OH, OH, AcO | 1.7 |

Biological Activity In Vivo

Analytical methodologies (LC/MS/MS) were developed that are capable of quantifying these acetate sugars and the resulting liberation of 2-DG in various biomatrices (plasma and brain tissue). Using this analytical method preliminary biodistribution studies were undertaken in CD-1 mice to examine the pharmacokinetics of these novel agents.

Briefly, four animals per treatment group were given equivalent doses of either 2-DG, the compound of Example 6 (6-O-acetate of 2-DG) or the compound of Example 4 (4,6-di-O-acetate of 2-DG) by oral gavage using the same vehicle. Individual groups of animals were then sacrificed at 0.25, 0.5, 1, 2 and 4 hours following dose administration. From each animal plasma and brain tissues were harvested and then analyzed for 2-DG content by LC/mass spectrometry.

Results from these studies demonstrate a clear and distinct difference in the delivery of the active compound to blood and brain. The peak plasma concentration of 2-DG delivered by the compound of Example 6 were more than twice that delivered by 2-DG alone (97 vs. 46 μg/ml). More importantly, the circulating half-life of 2-DG derived from the compound of Example 6 was double (1.2 vs. 0.6 hrs) that observed from the administration of 2-DG alone and the overall measure of drug exposure (area under the curve) was also twice that of 2-DG. These data demonstrate that the compound of Example 6 provides a more consistent and persistent exposure to the putative monosaccharide antimetabolite, providing active concentrations of 2-DG at the site of action (brain) for more than twice as long as when 2-DG is administered alone.

The compound of Example 4 performed even better. This compound provided mean plasma concentrations more than 6-fold>that observed with equivalent doses of 2-DG. Likewise peak brain tissue concentrations were also consistently greater (387.1 vs. 13.7 μg/gm) than for equivalent doses of 2-DG. This compound of Example 4 derived 2-DG exposure was of longer duration in the CNS as well, with 2-DG measurable in brain tissue for 8 times longer following the administration of this compound than with comparable 2-DG administration. In fact, at 2 hrs after 2-DG administration the highest attained brain tissue concentration was 12 μg/gm, while 4 hours after dosing with the compound of Example 4,2-DG concentrations of 256 μg/gm of brain tissue were observed.

We claim:

1. A method reducing, mitigating, or ameliorating cancer in a patient in need thereof comprising the step of administering to said patient a therapeutically effective amount of one or more compounds of the Formula I:

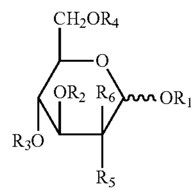

or a salt thereof, wherein $R_1$, $R_2$, $R_3$, and $R_4$ are each independently H, $COCH_3$, $COCH_2CH_3$, or $COCH_2CH_2CH_3$;

and $R_5$ and $R_6$ are each independently H or F ($^{18}F$ or $^{19}F$);

wherein at least one of $R_1$, $R_2$, $R_3$, and $R_4$ is $COCH_3$or $COCH_2CH_3$.

2. A method of inhibiting glycolysis in a patient in need thereof comprising the step of administering to said patient a therapeutically effective amount of one or more compounds of the Formula I:

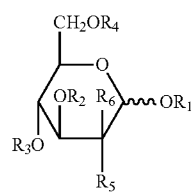

or a salt thereof, wherein $R_1$, $R_2$, $R_3$, and $R_4$ are each independently H, $COCH_3$, $COCH_2CH_3$, or $COCH_2CH_2CH_3$;

and $R_5$ and $R_6$ are each independently H or F ($^{18}F$ or $^{19}F$);

wherein at least one of $R_1$, $R_2$, $R_3$, and $R_4$ is $COCH_3$or $COCH_2CH_3$.

3. A compound of the structural formula:

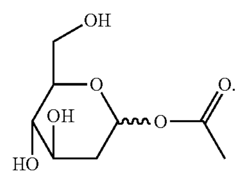

4. A compound of the structural formula:

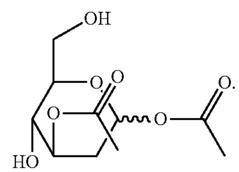 [SMILES: CC(=O)OC1CC(OC(C)=O)C(O)C(CO)O1]

5. A compound of the structural formula:
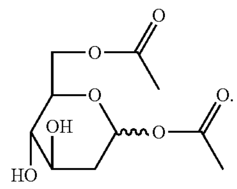
6. A compound of the structural formula:
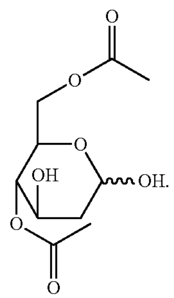
7. A compound of the structural formula:
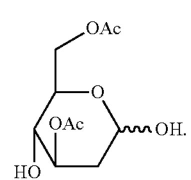
8. A compound of the structural formula:
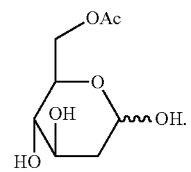
* * * * *